United States Patent [19]

Wolf et al.

[11] Patent Number: 5,147,645

[45] Date of Patent: Sep. 15, 1992

[54] PYRETHROIDS AND THEIR USE FOR CONTROLLING PESTS

[75] Inventors: Bernd Wolf, Mutterstadt; Hans Theobald, Limburgerhof; Winfried Zombik, Ilvesheim; Norbert Goetz, Worms; Jochen Wild, Deidesheim; Albrecht Harreus, Ludwigshafen; Peter Hofmeister, Neustadt; Christoph Kuenast, Ottenstadt; Jacobus J. DeKramer, Limburgerhof, all of Fed. Rep. of Germany

[73] Assignee: BASF Aktiengesellschaft, Ludwigshafen, Fed. Rep. of Germany

[21] Appl. No.: 590,690

[22] Filed: Oct. 1, 1990

Related U.S. Application Data

[63] Continuation of Ser. No. 367,738, Jun. 19, 1989, abandoned.

[30] Foreign Application Priority Data

Jun. 21, 1988 [DE] Fed. Rep. of Germany ....... 3820895

[51] Int. Cl.$^5$ .............................................. A01N 25/00
[52] U.S. Cl. ..................................... 424/405; 560/124
[58] Field of Search .......................... 560/124; 424/405

[56] References Cited

U.S. PATENT DOCUMENTS

T102,908  4/1983  Halpern et al. ..................... 560/124
3,927,068  12/1975  Searle et al. ........................ 560/124

FOREIGN PATENT DOCUMENTS 3327292  4/1984  Fed. Rep. of Germany .
2088369  6/1982  United Kingdom ................ 560/124

OTHER PUBLICATIONS

Elliot et al, Pestic. Sci., vol. 3, pp. 25-28 (1972).
Elliot et al., Pestic. Sco., vol. 1, pp. 49-52, (1970).

Primary Examiner—Lester L. Lee
Assistant Examiner—E. J. Kraus
Attorney, Agent, or Firm—Oblon, Spivak, McClelland, Maier & Neustadt

[57] ABSTRACT

Benzyl esters of the formula I

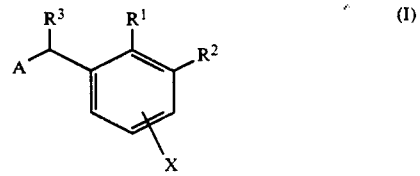

where $R^1$ is methyl, ethyl, halogen, methoxy or ethoxy, $R^2$ is alkyl, alkenyl, cycloalkyl, cycloalkenyl, bicycloalkyl, bicycloalkenyl, $C_1$-$C_5$-alkyl-substituted cycloalkyl, $C_1$-$C_5$-substituted cycloalkenyl, $C_1$-$C_5$-alkyl-substituted bicycloalkyl or $C_1$-$C_5$-alkyl-substituted bicycloalkenyl, $R^3$ is hydrogen, cyano, $C_2$-$C_4$-alkynyl, $C_2$-$C_4$-alkenyl or $C_1$-$C_4$-alkyl, A is the carboxylate radical of an acid component typical for pyrethroids and X is hydrogen or halogen, with the proviso that $R^2$ is not $CH_2$—CH=CH—B when B is hydrogen, alkyl or alkenyl and at the same time $R^1$ is methyl or halogen, and furthermore with the proviso that $R^2$ is not methyl when $R^1$ is methyl, their manufacture, their use for combating pests, and precursors for manufacturing the benzyl esters.

8 Claims, No Drawings

PYRETHROIDS AND THEIR USE FOR CONTROLLING PESTS

This is a continuation of application Ser. No. 07/367,738, filed on Jun. 19, 1989 and now abandoned.

The present invention relates to novel benzyl esters, processes for their preparation, pesticides which contain these esters as active ingredients and methods for controlling pests with these active ingredients and intermediates for the preparation of the novel benzyl esters.

It is known that certain esters of o,m-dimethylbenzyl alcohol have insecticidal properties [Pestic. Sci. 1 (2) (1970), 49–52; Pestic. Sci. 1 (5) (1970), 220–223; Pestic. Sci. 3 (1) (1972), 25–28; U.S. Pat. No. 4,332,815]. Furthermore, French Patent 2,531,074 and Pestic. Sci. 37 (6) (1986), 691–700 disclose some esters of o-methylbenzyl alcohols which carry an unsubstituted or terminally substituted allyl radical in the m-position. However, the insecticidal action of these esters is in most cases unsatisfactory under certain conditions (for example at low application concentrations). J. Agr. Food Chem. 29 (1981), 1118–1122 reports that 3-isopropylbenzyl 3-(2′,2′-dichlorovinyl)-2,2-dimethylcyclopropanecarboxylate has no insecticidal activity.

We have found that benzyl esters of the general formula I

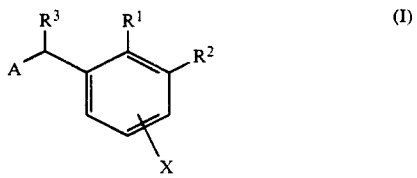

where $R^1$ is methyl, ethyl, halogen, methoxy or ethoxy, $R^2$ is alkyl, alkenyl, cycloalkyl, cycloalkenyl, bicycloalkyl, bicycloalkenyl, $C_1$–$C_5$-alkyl-substituted cycloalkyl, $C_1$–$C_5$-alkyl-substituted cycloalkenyl, $C_1$–$C_5$-alkyl-substituted bicycloalkyl or $C_1$–$C_5$-alkyl-substituted bicycloalkenyl, $R^3$ is hydrogen, cyano, $C_2$–$C_4$-alkynyl, $C_2$–$C_4$-alkenyl or $C_1$–$C_4$-alkyl, A is the carboxylate radical of an acid component typical for pyrethroids and X is hydrogen or halogen, with the proviso that $R^2$ is not $CH_2$—CH=CH—B when B is hydrogen, alkyl or alkenyl and at the same time $R^1$ is methyl or halogen, and furthermore with the proviso that $R^2$ is not methyl when $R^1$ is simultaneously methyl, have a powerful insecticidal and acaricidal action.

Unless stated otherwise, for the purposes of the present invention the terms below have the following meanings:

Alkyl is straight-chain or branched alkyl of 1 to 20, in particular 1 to 12, carbon atoms. Examples are methyl, ethyl, propyl, isopropyl, n-butyl, isobutyl, secbutyl and tert-butyl.

Alkenyl is a straight-chain or branched, ethylenically unsaturated hydrocarbon group having 2 to 20 carbon atoms and 1 to 10 ethylenic bonds, in particular having 2 to 12 carbon atoms and 1 to 5 ethylenic bonds. Examples are vinyl, isopropenyl, 1-butenyl, 1,5-hexadienyl, 1-methylpropenyl and 1-ethylvinyl.

Cycloalkyl is cycloalkyl having 3 to 8, in particular 3 to 6, carbon atoms in the ring, such as cyclopropyl, cyclobutyl, cyclopentyl or cyclohexyl. This cycloalkyl group is unsubstituted or substituted by one or more, for example from 1 to 4, branched or straight-chain $C_1$–$C_5$-alkyl radicals, such as methyl, ethyl, propyl, isopropyl, butyl, sec-butyl, tert-butyl or pentyl. Examples are 3,5-diethylcyclohexyl and tetramethylcyclopropyl.

Cycloalkenyl is cycloalkenyl having 3 to 8, in particular 3 to 6, carbon atoms in the ring, such as cyclopropenyl, cyclobutenyl, cyclopentenyl, cyclopentadienyl or cyclohexadienyl. The cycloalkenyl group is unsubstituted or substituted by one or more, for example from 1 to 4, branched or straight-chain $C_1$–$C_5$-alkyl radicals, such as methyl, ethyl, propyl, isopropyl, butyl, sec-butyl, tert-butyl or pentyl. Examples are 1-cyclopentenyl, 1-cyclohexenyl, 3,5-dimethyl-1-cyclohexenyl and 1,3-cyclohexadienyl.

Bicycloalkyl is bicycloalkyl having 5 to 12, in particular 6 to 8, carbon atoms in the bicyclic structure, such as 2-norbornyl or bicyclo[4.1.0]hept-1-yl. This bicyclic structure is unsubstituted or substituted by one or more, for example 1 or 2, branched or straight-chain alkyl radicals, such as methyl, ethyl, propyl, isopropyl, butyl, sec-butyl or pentyl. An example is 2,6-dimethylbicyclo[4.1.0]hept-1-yl.

Bicycloalkenyl is an unsaturated bicycloalkyl group having 5 to 12, in particular 6 to 8, carbon atoms in the bicyclic structure and one or more, for example 1 or 2, ethylenic double bonds, for example norbornen-2-yl or norbornadien-2-yl. This bicycloalkenyl group is unsubstituted or substituted by one or more, for example from 1 to 3, branched or straight-chain $C_1$–$C_5$-alkyl radicals, such as methyl, ethyl, propyl, isopropyl, butyl, secbutyl or pentyl. An example is 7,7-dimethylbicyclo[4.1.0]hept-2-en-1-yl.

In these compounds, $R^1$ is preferably methyl bromine, chlorine or fluorine, $R^2$ is preferably a branched alkyl or alkenyl radical of 3 to 8 carbon atoms, such as isopropyl, isopropenyl, sec-butyl, tert-butyl, 1-buten-2-yl, 2-butenyl, 1,3-butadienyl, isopentyl, sec-pentyl, 3-penten-2-yl, 1-penten-2-yl or sec-hexyl, the three first-mentioned radicals being particularly preferred, $C_3$–$C_8$-cycloalkyl or cycloalkenyl, such as cyclopentyl, 1-cyclopentenyl, cyclohexyl, 1-cyclohexenyl or, in particular, cyclopropyl, or $C_6$–$C_8$-bicycloalkyl or bicycloalkenyl, such as 2-norbornyl, 2-norbornen-2-yl or 2,5-norbornadien-2-yl, $R^3$ is hydrogen, ethynyl or cyano, X is hydrogen or fluorine and A is a carboxylate radical II, III or IV

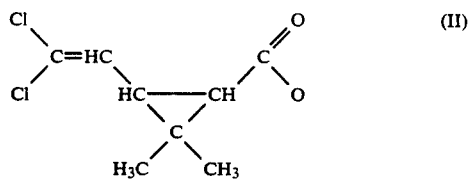

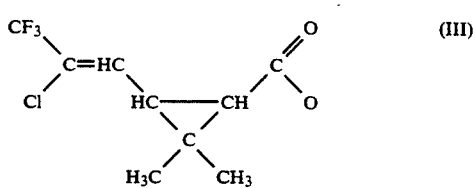

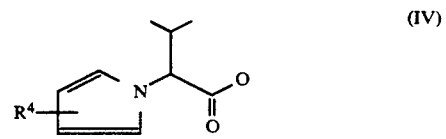

and $R^4$ is hydrogen, $C_1$-$C_4$-alkyl or $C_1$-$C_4$-haloalkyl, such as methyl, ethyl, propyl, isopropyl, butyl, isobutyl, secbutyl, tert-butyl, trifluoromethyl, trichloromethyl or 2,2,2-trifluoroethyl.

The esters of the general formula I can be obtained by reacting an acid A-H or a derivative of this acid, such as an acyl chloride, an anhydride or the like, with a benzyl alcohol of the general formula V or a derivative of V in accordance with the following equation.

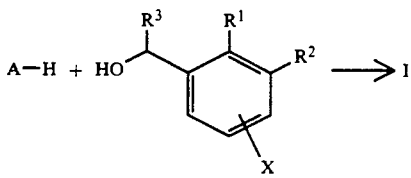

($R^1$, $R^2$, $R^3$, X and A have the meanings stated in claim 1).

The reaction can be accelerated in a conventional manner by adding a catalyst, such as sulfuric acid, hydrogen halide, a sulfonic acid of an acidic ion exchanger, and the equilibrium in the esterification reaction can be shifted in the desired direction by removing water or the ester I from the reaction mixture, for example by azeotropic distillation or by binding the water to sulfuric acid or a hydrohalic acid.

It is also possible to react the corresponding acyl chlorides with the alcohols of the formula V in the presence of an acid acceptor (cf. Houben-Weyl, Methoden der organischen Chemie, Volume VIII, page 541 et seq., Georg-Thieme-Verlag, Stuttgart 1952).

Suitable acid acceptors are the conventional basic agents, in particular aliphatic, aromatic and heterocyclic amines, e.g. triethylamine, dimethylamine, piperidine, dimethylaniline, dimethylbenzylamine, pyridine and 2-picoline.

The reaction can be carried out in a solvent or diluent. The stated acid acceptors themselves or, for example, the following solvents or diluents or mixtures of these are suitable for this purpose: aliphatic and aromatic hydrocarbons and chlorohydrocarbons, such as petroleum ether, benzene, toluene, xylene, gasoline, dichloromethane, chloroform, tetrachloromethane, 1,2-dichloroethane or chlorobenzene, ethers, such as diethyl ether, di-n-butyl ether, methyl tert-butyl ether, tetrahydrofuran or dioxane, ketones, e.g. acetone, methyl ethyl ketone or methyl isopropyl ketone, and nitriles, such as acetonitrile or propionitrile.

The starting materials are usually used in a stoichiometric ratio. An excess of one or other of the starting materials may however be quite advantageous in specific cases.

The reaction usually takes place at an adequate rate at above 0° C. Since it is generally exothermic, it may be advantageous to provide a means of cooling.

In some cases, it is useful and advantageous to esterify the compounds of the formula V in situ, particularly when $R^3$ in the general formula V is cyano.

The novel esters may furthermore be prepared by virtually any known method of ester synthesis, for example by reacting a corresponding anhydride with an alcohol of the formula V, by reacting a corresponding salt with the derivative of an alcohol of the formula V or by transesterification (cf. Houben-Weyl, loc. cit., pages 508–628).

Where $R^1$ is methyl or ethyl, the alcohols of the general formula V which are required as starting materials can be obtained by reacting a correspondingly substituted benzaldehyde with i) a reducing agent if $R^3$ is H, ii) hydrocyanic acid or a metal cyanide in the presence or absence of an acid, if $R^3$ is CN, or iii) a metalorganyl $MeR^3$ or $R^3MeHal$ if $R^3$ is $C_2$-$C_4$-alkynyl, $C_2$-$C_4$-alkenyl or $C_1$-$C_4$-alkyl, Me being an alkali metal, alkaline earth metal or transition metal and Hal being halogen.

Suitable reducing agents are all conventional reducing agents which convert benzaldehydes in benzyl alcohols (Houben-Weyl, Methoden der organischen Chemie, Volume VI/1b, pages 1–500, 1984 Edition, Georg Thieme Verlag, Stuttgart). In addition to catalytic hydrogenation, nonmetallic reducing agents and metal hydrides, complex metal hydrides, eg. lithium aluminum hydride or sodium borohydride, are particularly useful. Cathodic and photochemical reduction are also suitable.

For the preparation of the cyanohydrins, the benzaldehydes are reacted with hydrocyanic acid, with hydrocyanic acid produced in situ from metal cyanides or with metal cyanides, in the presence of an alkali metal bisulfite solution, if necessary a basic catalyst, such as potassium carbonate, or a phase transfer catalyst, eg. benzyltriethylammonium chloride, being added.

Preferably used metal cyanides are alkali metal cyanides, eg. sodium cyanide or potassium cyanide.

The reaction is carried out in a conventional manner, for example as described in Houben-Weyl, Methoden der organischen Chemie, Volume VIII, pages 274–278, 1952 Edition, and Volume E5, page 1413 et seq, 1985 Edition.

Suitable metalorganyls are the corresponding organometallic compounds, in particular lithiumorganyl compounds $LiR^3$, such as methyllithium, ethyllithium or butyllithium, or the corresponding Grignard compounds $R^3MgHal$, where Hal is chlorine, bromine or iodine, eg. methylmagnesium bromide, ethylmagnesium chloride propylmagnesium iodide or vinylmagnesium iodide.

The reaction with metalorganyls can be carried out in a conventional manner, for example as described in Houben-Weyl, Methoden der organischen Chemie, Volume 13/2a, page 285 et seq, 1973, in an inert organic solvent, such as ether or tetrahydrofuran, under a protective gas, so that further information in this respect is unnecessary.

The benzaldehydes are prepared by reacting an appropriately substituted benzonitrile with a reducing agent to give an aldimine and hydrolyzing the latter in a conventional manner.

The reaction sequence is shown in the following reaction scheme:

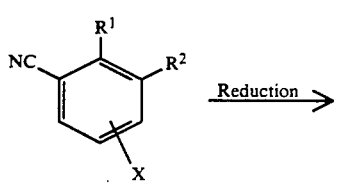

-continued

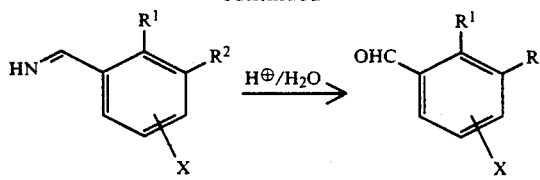

In addition to hydrogen (catalytic hydrogenation) and tetrachlorostannous (II) acid, particularly suitable reducing agents are aluminum hydrides, eg. diisopropylaluminum hydride (cf. Houben-Weyl, Methoden der organischen Chemie, Volume E3, pages 476–488, Georg Thieme Verlag, Stuttgart). The aldimines are generally hydrolyzed by treatment with a dilute or concentrated mineral acid, such as hydrochloric acid. In the case of sensitive aldehydes, it is advisable to use buffered acetic acid.

It is not absolutely essential to isolate the aldimines. They can advantageously be hydrolyzed immediately to the benzaldehydes Ib, without working up and purification.

For the preparation of the benzonitriles, an appropriately substituted chloro- or bromobenzene is reacted with a metal cyanide in an organic solvent in accordance with the following equation:

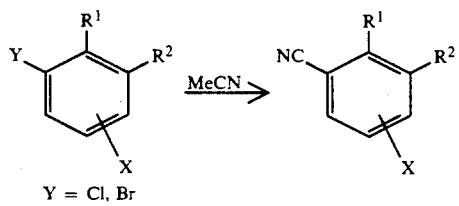

Y = Cl, Br

Suitable metal cyanides (MeCN) are alkali metal, alkaline earth metal and heavy metal cyanides (Houben-Weyl, Methoden der organischen Chemie, Volume E5, pages 1447–1467, 1985 Edition, Georg Thieme Verlag, Stuttgart). The use of copper(I) cyanide is particularly advantageous. The reaction takes place smoothly in aprotic, polar solvents. Dimethylformamide, pyridine, 1-methyl-2-pyrrolidone and phosphoric acid tris-(dimethylamide) are particularly suitable.

The reaction is advantageously carried out at from 100° to 250° C. Where copper(I) cyanide is used, the reaction mixture is worked up (the initially formed nitrile/copper halide/copper cyanide complexes are destroyed) with iron(III) chloride/hydrochloric acid, 1,2-diaminoethane or sodium cyanide. The use of 1,2-diaminoethane is advantageous.

Typical examples of the chloro- or bromobenzene derivatives, such as 2-chloro-6-n-butyltoluene, 3-chloro-2-methylstyrene, 1-chloro-2-methyl-3-(1′-propenyl)benzene, 2,3-dimethylchlorobenzene, 2,3-dimethylbromobenzene, 4-fluoro-2,3-dimethylbromobenzene, 1,2-dichloro-3,4-dimethylbenzene, 1,5-dichloro-2,3-dimethylbenzene and 1,4-dichloro-2,3-dimethylbenzene, are disclosed in U.S. Pat. No. 4,538,003; European Patent 80,359; J. Med. Chem. 28 (10), 1436–1440; J. Chromatogr. 370 (3) (1986), 355–376; Gazz. Chim. Hal. 103 (8–9) (1973), 1019–1025 or Chem.-Ztg. 103 (1) (1979), 1–7.

A general synthesis method for the preparation of these compounds, where $R^1$, $R^2$, X and Y have the above-mentioned meanings, starts from dichloro-, dibromo-, dibromochloro-, dibromofluoro- or dichlorofluorobenzene derivatives and is illustrated by the following reaction scheme:

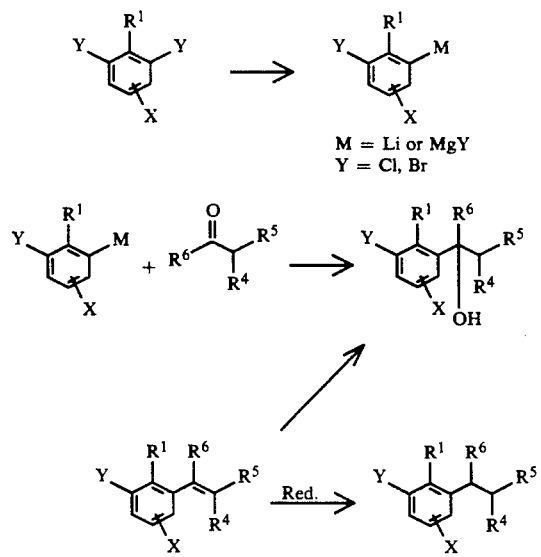

In this reaction scheme, the side chains

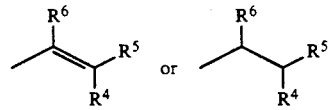

correspond to the radical $R^2$. $R^4$, $R^5$ and $R^6$ are each hydrogen, branched or straight-chain alkyl or branched or straight-chain alkenyl. $R^4$ and $R^6$ or $R^5$ and $R^6$ may furthermore be bonded to form a ring, which is unsubstituted or substituted by $C_1$–$C_5$-alkyl, or $R^4$, $R^5$ and $R^6$ are such that a bicyclic ketone is obtained, the said ketone being unsubstituted or substituted by $C_1$–$C_5$-alkyl.

Di- or trihalobenzenes where $R^1$ is methyl or ethyl, X is hydrogen, chlorine or fluorine and Y is chlorine or bromine are converted into the monometalorganyls. The conventional preparation processes which start from aryl halides (cf. Houben-Weyl, Methoden der organischen Chemie, Volume XIII/1, page 134 et seq, 1970 Edition, and Volume XIII/2a, page 54 et seq., 1973 Edition, Georg Thieme Verlag, Stuttgart), are suitable for the preparation of the organolithium or Grignard compounds. Where Y is chlorine and X is hydrogen, the synthesis of the Grignard compounds requires higher reaction temperatures. The use of tetrahydrofuran at the boil has proven particularly useful.

The organometallic compounds are reacted with carbonyl compounds VI where $R^4$ to $R^6$ have the above-mentioned meanings to give benzyl alcohols. The latter are dehydrated to give styrenes, the methods described in Houben-Weyl (Methoden der organischen Chemie, Volume V/Ib, page 45 et seq., 1972 Edition, Georg-Thieme-Verlag, Stuttgart) being suitable. The use of acidic dehydrating agents, in particular oxalic acid or p-toluenesulfonic acid, with simultaneous removal of the resulting water by means of a separator is advantageous.

The styrene derivatives obtained in the manner described above are either used directly for the preparation of the benzonitriles or reduced beforehand. This reduction may be carried out either by noncatalytic reduction (for example with ethanol and sodium) or by catalystic hydrogenation (cf. Houben-Weyl, Methoden der organischen Chemie, Volume V/1a, page 405 et seq., 1970 Edition, Georg Thieme Verlag, Stuttgart). Examples of suitable catalysts are $PtO_2$, Raney nickel, Pd/carbon, $Pd/CaCO_3$, copper chromite or $Pd/Al_2O_3$. The use of Pd/carbon has proven particularly useful. Suitable solvents are alcohols, eg. methanol, ethanol or isopropanol, ethers, eg. tetrahydrofuran or dioxane, and esters, eg. ethyl acetate. The use of ethanol is advantageous. The catalystic hydrogenation is carried out, as a rule, at room temperature and under from 1 to 150 bar. The small amounts of compounds in which a halogen/- hydrogen exchange additionally takes place are often formed as byproducts.

Benzyl alcohols of the general formula V where $R^1$ is halogen and $R^3$ is hydrogen can advantageously be prepared by electrochemical oxidation of a toluene derivative (cf. also U.S. Pat. No. 3,448,021 or J. Org. Chem. 51 (1986), 4544) in the presence of an alkanoic acid, eg. formic, acetic or propionic acid, to give a benzyl ester, followed by hydrolysis of the benzyl ester in accordance with the following equation:

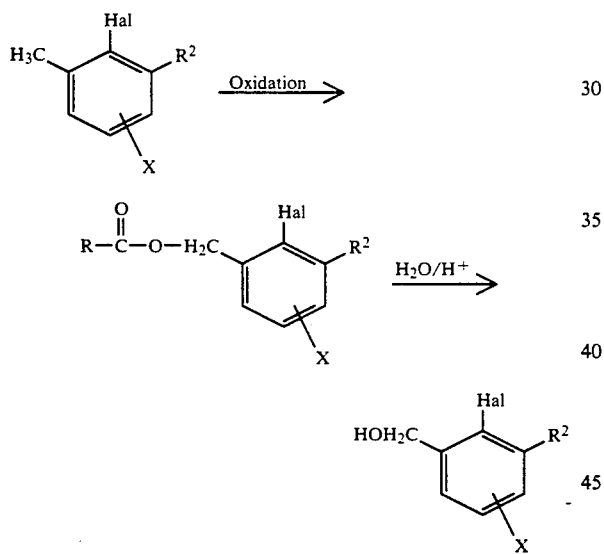

R = $C_1$-$C_3$-alkyl

The electrochemical oxidation can be carried out in a conventional electrolysis cell, undivided flow-through cells preferably being used. The anode materials used are, for example, noble metals, such as platinum, or oxides, such as $RuO_2$, $Cr_2O_3$ or $TiO_x/RuO_x$; graphite is particularly preferably used. Cathode materials may include iron, steel, nickel, noble metals, such as platinum, and graphite. The electrolyte used is a solution of the toluene in the alkanoic acid, to which electrolyte an auxiliary electrolyte has been added to increase the conductivity. Furthermore, the solubility of the toluene may be increased by adding a cosolvent. Examples of cosolvents are ketones, such as acetone or methyl ethyl ketone, nitriles, such as acetonitrile or propionitrile, and anhydrides, such as acetic anhydride. The auxiliary electrolytes used may be the conductive salts usually employed in electrochemistry, for example fluorides, tetrafluoborates, sulfonates or alkylsulfates.

The electrolyte has, for example, the following composition:
1-20% of a toluene of the general formula II,
1-10% of a conductive salt,
0-20% of a cosolvent and
50-95% of an alkanoic acid.

The current densities and electrolysis temperatures can be varied within wide limits. For example, electrolysis is carried out at 0.2-20 $A/dm^2$ and at from 15° to 95° C. The toluenes used can be converted to a substantial extent and the discharged electrolysis mixtures are worked up by conventional methods, for example by distillation, extraction and crystallization. The cosolvent, excess alkanoic acid and the conductive salt can be separated off from the benzyl esters and, together with any unconverted toluene, can be recycled to the electrolysis.

Benzyl alcohols of the general formula V where $R^3$ is cyano, alkynyl, alkenyl or alkyl of 1 or 2 to 4 carbon atoms and $R^1$ is halogen can be prepared starting from a benzaldehyde of the general formula VI

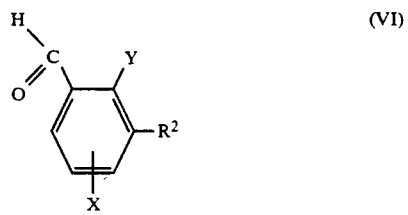

where Y is halogen and $R^2$ and X have the meanings stated in claim 1. In this process,
a) if $R^3$ is cyano, the benzaldehyde VI is reacted with hydrocyanic acid or a metal cyanide in the presence or absence of an acid, and
b) if $R^3$ is alkynyl, alkenyl or alkyl of not more than 4 carbon atoms, the aldehyde VI is reacted with a corresponding metalorganyl $R^3$-M.

Preferably used metal cyanides are alkali metal cyanides, e.g. sodium cyanide or potassium cyanide, if necessary an auxiliary reagent, for example $NaHSO_3$, or a phase transfer catalyst being added to the two-phase system.

Suitable metalorganyls are the corresponding organometallic compounds with metals of main group 1, and the corresponding Grignard compounds.

The benzaldehydes of the general formula VI can be prepared starting from the corresponding benzyl alcohols V by methods known from the literature (Houben-Weyl, Methoden der organischen Chemie, Volume E3, page 265 et seq), for example by oxidation with $MnO_2$.

For the preparation of benzyl alcohols of the general formula V where $R^1$ is methoxy or ethoxy, a phenol of the general formula VII

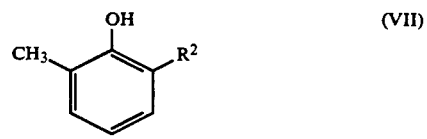

is used as a starting material. The phenols VII can be alkylated by the methods described in Houben-Weyl (Methoden der organischen Chemie, Volume VI/3, page 49 et seq., Georg-Thieme-Verlag, Stuttgart, 1965). The subsequent conversion of the methyl group into the hydroxymethyl radical is effected either electrochemically or via the corresponding benzyl halide as an intermediate. The benzyl halides can also be used directly for the preparation of the novel esters.

Another method for the synthesis of benzyl alcohols of the general formula V where $R^1$ is methoxy or ethoxy starts from a hydroxybenzoic acid of the general formula VIII, which is converted into an alkoxybenzoate IX by double alkylation with an alkyl halide $R^5$-Hal

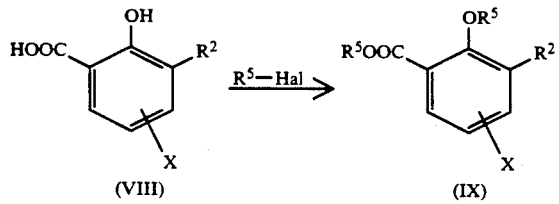

(where $R^5$ is $CH_3$ or $C_2H_5$ and Hal is Cl, Br or I) or with another conventional alkylating agent (cf. Houben-Weyl, Methoden der organischem Chemie, Volume 6/III, page 49 et seq., 1965 Edition, and Volume 8/III, page 541 et seq., 1952 Edition, Georg-Thieme-Verlag, Stuttgart). The esters IX can be converted into the desired benzyl alcohols of the general formula V where $R^1$ is methoxy or ethoxy in a conventional manner by reduction (for example with a complex hydride, such as lithium aluminum hydride). Starting from these alcohols and using methods known from the literature (Houben-Weyl, Methoden der organischen Chemie, Volume E3, page 265 et seq.), it is also possible to prepare the corresponding benzaldehydes X, which can be converted into α-substituted benzyl alcohols XI by the methods described for the benzaldehydes VI.

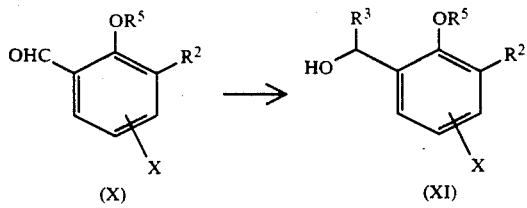

The pyrethroid acids used and their derivatives are described, for example, in Wegler, Chemie der Pflanzenschutz- and Schädlingsbekämpfungsmittel, Volume 7, Springer Verlag, Berlin, Heidelberg, New York 1981.

Typical acids of the formula A-H are listed below, although this list is not intended to impose any restriction:

$A^1$-H: 3-(2',2'-dimethylvinyl)-2,2-dimethylcyclopropane-1-carboxylic acid
$A^2$-H: 3-(2',2'-dichlorovinyl)-2,2-dimethylcyclopropane-1-carboxylic acid
$A^3$-H: 3-(2'-chloro-3',3',3'-trifluoroprop-1'-enyl)-2,2-dimethylcyclopropane-1-carboxylic acid
$A^4$-H: 3-(2',2'-dibromovinyl)-2,2-dimethylcyclopropane-1-carboxylic acid
$A^5$-H: 3-(2',2'-difluorovinyl)-2,2-dimethylcyclopropane-1-carboxylic acid
$A^6$-H: 3-(2'-fluoro-3',3',3'-trifluoroprop-1'-enyl)-2,2-dimethylcyclopropane-1-carboxylic acid
$A^7$-H: 3-(2',2'-bistrifluoromethylvinyl)-2,2-dimethylcyclopropane-1-carboxylic acid
$A^8$-H: 2-(4'-chlorophenyl)-3-methylbutyric acid
$A^9$-H: 2-(4'-fluorophenyl)-3-methylbutyric acid
$A^{10}$-H: 2-(4'-difluoromethoxyphenyl)-3-methylbutyric acid
$A^{11}$-H: 3-(4'-tert-butylphenyl)-2,2-dimethylcyclopropane-1-carboxylic acid
$A^{12}$-H: 2,2,3,3-tetramethylcyclopropane-1-carboxylic acid
$A^{13}$-H: 1-(4'-chlorophenyl)-cyclopropane-1-carboxylic acid
$A^{14}$-H: 1-(4'-ethoxyphenyl)-2,2-dichlorocyclopropane-1-carboxylic acid
$A^{15}$-H: 3-[2'-(4''-chlorophenyl)-2'-chlorovinyl-2,2-dimethylcyclopropane-1-carboxylic acid
$A^{16}$-H: 3-(1',3'-butadienyl)-2,2-dimethylcyclopropane-1-carboxylic acid
$A^{17}$-H: 3-(2'-methyl-2'-methoxycarbonylvinyl)-2,2-dimethylcyclopropane-1-carboxylic acid
$A^{18}$-H: 2-(2'-chloro-4'-trifluoromethylphenylamino)-3-methylbutyric acid
$A^{19}$-H: 2-(2'-fluoro-4'-trifluoromethylphenylamino)-3-methylbutyric acid
$A^{20}$-H: 3-methyl-2-(4'-trifluoromethylphenylamino)-butyric acid
$A^{21}$-H: 3-methyl-2-(pyrrol-1'-yl)-butyric acid
$A^{22}$-H: 3-methyl-2-(3'-methylpyrrol-1'-yl)-butyric acid
$A^{23}$-H: 2-(3',4'-dimethylpyrrol-1'-yl)-3-methylbutyric acid
$A^{24}$-H: 2-(2',5'-dimethylpyrrol-1'-yl)-3-methylbutyric acid
$A^{25}$-H: 2-(isoindolin-2-yl)-3-methylbutyric acid
$A^{26}$-H: 1,1-dimethyl-2,2[H]indenespirocyclopropane-3-carboxylic acid
$A^{27}$-H: 3-cyclopentylidenemethyl-2,2-dimethylcyclopropane-1-carboxylic acid
$A^{28}$-H: 3-(1',2'-dibromo-2',2'-dichloroethyl-2,2-dimethylcyclopropane-1-carboxylic acid
$A^{29}$-H: 3-methyl-2-(pyrazol-1'-yl)-butyric acid
$A^{30}$-H: 3-methyl-2-(imidazol-1'-yl)-butyric acid Of course, the compounds of the formula I may in any case occur in the form of pure diastereomers or one or more pairs of optical antipodes and in many cases in the form of a plurality of diastereomers and can be used as active ingredients, which, depending on the starting materials and the reaction conditions, occur in pure form or as mixtures. The mixtures can be separated in a conventional manner into their sterically pure constituents; their biological action is dependent on their steric configuration in individual cases.

The benzyl esters of the formula I are suitable for effectively combating pests from the class of insects, mites and nematodes. They may be used as pesticides in crop protection, and in the hygiene, stores protection and veterinary sectors.

Examples of injurious insects from the Lepidoptera order are *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grndiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Heliothis zea, Hellula undalis, Hibernia defoliaria, Hyphantria cunea, Hyphantria cunea, Hyponomeuta malinellus, Keifferia lycopersicella, Lambdina fiscellaria, Laphygma exigua, Leucoptera coffeella,*

Leucoptera scitella, Lithocolletis blancardella, Lobesia botrana, Loxostege sticticalis, Lymantria dispar, Lymantria monacha, Lyonetia clerkella, Malacosoma neustria, Mamestra brassicase, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni and Zeiraphera canadensis.

Examples from the Coleoptera order are Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyliotreta striolata, Popillia japonica, Sitona lineatus and Sitophilus granaria.

Examples from the Diptera order are Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea and Tipula paludosa.

Examples from the Thysanoptera order are Frankliniella fusca, Frankliniella occidentalis, Frankliniella tritici, Scirtothrips citri, Thrips oryzae, Thrips palmi and Thrips tabaci.

Examples from the Hymenoptera order are Athalia rosae, Atta cephalotes, Atta sexdens, Atta texana, Hoplocampa minuta, Hoplocampa testudinea, Monomorium pharaonis, Solenopsis geminata and Solenopsis invicta.

Examples from the Heteroptera order are Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis and Thyanta perditor.

Examples from the Homoptera order are Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulacorthom pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappahphis mali, Schizaphis graminum, Schizoneura lanuginosa, Trialeurodes vaporariorum, and Viteus vitifolii.

Examples from the Isoptera order are Calotermes flavicollis, Leucotermes flavipes, Reticulitermes lucifugus, and Termes natalensis.

Examples from the Orthoptera order are Acheta domestica, Blatta orientalis, Blattella germanica, Forficula auricularia, Gryllotalpa gryllotalpa, Locusta migratoria, Melanoplus birittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus and Tachycines asynamorus.

Examples of Acarina from the Arachnida class are Amblyomma americanum, Amyglyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodoorus moubata, Otobins megnini, Paratetranychus pilosus, Permanyssus gallinae, Phyllocaptrata oleivora, Polyphagotarsonemus latus, Psoroptes ovis, Rhipicephalus appendiculatus, Rhipicephalus evertsi, Saccoptes scabiei, Tetranychus cinnabarinus, Tetranychus kanzawai, Tetranychus pacificus, Tetranychus telarius and Tetranychus urticae.

Examples from the Nemathelminthes class are root-knot nematodes, such as Meloidogyne hapla, Meloidogyne incognita, Meloidogyne javanica, Zysten bildende Nematoden, z.B. Globodera rostochiensis, Heterodera avenae, Hetrodera glycinae, Heterodera schatii, Hetrodera triflolii, and stem and leaf eelworms, such as Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Paratylenchus neglectus, Paratylenchus penetrans, Paratylenchus curvitatus, and Paratylenchus goodeyi.

The active ingredients may be applied for instance as such, or in the form of formulations or application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of formulations are given below.
I. 5 parts by weight of compound no. 1 is intimately mixed with 95 parts by weight of particulate kaolin. A dust is obtained containing 5% by weight of the active ingredient.
II. 30 parts by weight of compound no. 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.
III. 10 parts by weight of compound no. 3 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.
IV. 20 parts by weight of compound no. 4 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.
V. 80 parts by weight of compound no. 5 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90, % by weight of active ingredient.

The active ingredient concentrations in the finished formulations may vary over a wide range. Generally, they are from 0.0001 to 10, and preferably from 0.01 to 1, %. The active ingredients may also successfully be used in the ultra-low-volume (ULV) method, where it is possible to apply formulations containing more than 95 wt % of active ingredient, or even the active ingredient without additives.

In the open, the amount of active ingredient applied is for example from 0.01 to 10, particularly from 0.05 to 2, kg/ha.

There may be added to the active ingredients (if desired, immediately before use (tankmix)) oils of various types, herbicides, fungicides, other pesticides and bactericides. These agents may be added to the active ingredients according to the invention in a weight ratio of from 1:10 to 10:1.

The compounds according to the invention are manufactured in accordance with the following examples or by appropriate modification thereof.

MANUFACTURING EXAMPLE 1 cis,trans-3-(2',2'-Dichlorovinyl)-2,2-dimethylcyclopropane-1-carboxylic acid-(3-isopropenyl-2-methylbenzyl)-ester At 20° C., 4.55 g of 3-(2',2'-dichlorovinyl)-2,2-dimethylcyclopropane-1-carboxylic acid chloride is added dropwise to 3.1 g of 3-isopropenyl-2-methylbenzyl alcohol and 1.95 g of 2-picoline in 20 ml of toluene. After the exothermic reaction has subsided, the mixture is allowed to react for 5 hours, after which it is poured through a filter filled with silica gel, followed by rinsing with toluene. After the solvent has been distilled off there is obtained 6.4 g of a pale yellow oil ($n^{21}$:1.5349).

Analysis: Calc. C, 64.60; H, 6.28; O 9.06; Cl, 20.07. Found C, 64.80; H, 6.40; O 9.20; Cl, 19.90.

300 MHz NMR spectrum in CDCl$_3$: δ (ppm)=1.15–1.35 (6H); 1.68; 1.91; 2.02 and 2.28 (2H); 2.0 (3H); 2.3 (3H); 4.83 (1H); 5.17 (2H); 5.2 (1H); 5.62 and 6.3 (1H); 7.08–7.27 (3H).

MANUFACTURING EXAMPLE 2 cis-3-(2'-Chloro-3',3',3'-trifluoroprop-1'-enyl)-2,2-dimethylcyclopropane-1-carboxylic acid-(3-isopropyl-2-methylbenzyl)-ester and
trans-3-(2'-chloro-3',3',3'-trifluoroprop-1'-enyl)-2,2-dimethylcyclopropane-1-carboxylic acid-(3-isopropyl-2-methylbenzyl)-ester At 20° C., 6.8 g of 3-(2'-chloro-3',3',3'-trifluoroprop-1'-enyl)-2,2-dimethylcyclopropane-1-carboxylic acid chloride (cis:trans=1:1) is added dropwise to 4.1 g of 3-isopropyl-2-methylbenzyl alcohol and 2.4 g of 2-picoline in 30 ml of toluene. After the exothermic reaction has subsided the mixture is allowed to afterreact for 5 hours. The mixture is then purified by column chromatography over silica gel with toluene/cyclohexane (3/7) and at the same time separated into the cis and trans benzyl esters (Example 2a=cis compound, Example 2b=trans compound).

300 MHz NMR spectrum in CDCl$_3$:

cis compound (2a): δ (ppm)=1.22–1.37 (12H); 2.05 (1H); 2.1 (1H); 2.33 (3H); 3.25 (1H); 5.17 (2H); 6.99 (1H); 7.15–7.32 (3H).

trans compound (2b): δ (ppm)=1.18–1.38 (12H); 1.82 (1H); 2.32 (3H); 2.44 (1H); 3.23 (1H); 5.2 (2H); 6.14 (1H); 7.15–7.32 (3H).

Analysis of the cis compound: Calc. C, 61.78; H, 6.22; F, 14.66; Cl, 9.12. Found C, 61.8; H, 6.3; F, 14.8; Cl, 9.1.

MANUFACTURING EXAMPLE 3

3-(2',2'-dibromovinyl)-2,2-dimethylcyclopropane-1-carboxylic acid-[3-(1'-cyclohexenyl)-2-methyl-α-cyanobenzyl]-ester A solution of 1.56 g of potassium cyanide and 0.5 ml of benzyldimethyldodecylammonium chloride (Lutensit ®) in 15 ml of water, and 6.95 g of 3-(2',2'-dibromovinyl)-2,2-dimethylcyclopropane-1-carboxylic acid chloride are added to 4 g of 3-(1'-cyclohexenyl)-2-methylbenzaldehyde in 100 ml of ether. The mixture is stirred for 15 hours at room temperature, the organic phase is separated off, washed with water and dried over sodium sulfate, and the solvent is stripped off.

There is obtained 10.4 g of an oil which gives, after purification by column chromatography, 7.3 g of pure compound.

Analysis: Calc. C, 54.56; H, 4.97; O 6.31; N, 2.76; Br, 31.5. Found C, 55.0; H, 5.0; O 6.5; N, 2.8; Br, 31.2.

200 MHz NMR spectrum in CDCl$_3$: δ (ppm)=1.21–1.4 (6H); 1.6–2.3 (2H); 1.77 (4H); 2.21 (4H); 2.34 (3H); 5.6 (1H); 6.22 and 6.76 (1H); 7.2–7.34 (2H); 7.5–7.6 (1H).

MANUFACTURING EXAMPLE 4

3-Methyl-2-(pyrrol-1'-yl)-butyric acid-(2-chloro-3-isopropylbenzyl)-ester a) At room temperature, 29.8 g of thionyl chloride is carefully dripped into 35 g of 2-chloro-3-isopropylbenzyl alcohol in 80 ml of carbon tetrachloride. The mixture is stirred for 15 hours at 25° C. and then evaporated down. Distillation (bp $_{0.3}$:76°–78° C.) gives 33 g of 2-chloro-3-isopropylbenzyl chloride.

b) 7.6 g of sodium methylate solution (30% strength) is added to a solution of 7 g of 3-methyl-2-(pyrrol-1'-yl)-butyric acid in 100 ml of absolute methanol. The solvent is distilled off, 100 ml of acetonitrile is added to the residue, 8 g of 2-chloro-3-isopropylbenzyl chloride is introduced and the whole is stirred for 7 hours at 80° C. The solvent is distilled off under pressure, and the residue is taken up in ether and washed with water.

After drying over sodium sulfate and distilling off the solvent there is obtained 10 g of crude product. Purification by column chromatography over silica gel using toluene as eluant gives 3.8 g of the pure benzyl ester.

200 MHz NMR spectrum in CDCl$_3$: δ (ppm)=0.74 (3H); 0.99 (3H); 1.23 (6H); 2.43 (1H); 3.45 (1H); 4.2 (1H); 5.27 (2H); 6.17 (2H); 6.82 (2H); 7.09–7.33 (3H).

MANUFACTURING EXAMPLE 5 cis,trans-3-(2'-Chloro-3',3',3'-trifluoroprop-1'-enyl)-2,2-dimethylcyclopropane-1-carboxylic acid-(2-fluoro-3-isopropylbenzyl)-ester At room temperature, 7.8 g of 3-(2'-chloro-3',3',3'-trifluoroprop-1'-enyl)-2,2-dimethylcyclopropane-1-carboxylic acid chloride is added dropwise to 5.1 g of 2-fluoro-3-isopropylbenzyl alcohol and 4 g of triethylamine in 100 ml of toluene. After the exothermic reaction has subsided, the mixture is stirred for 4 hours at 60° C. After cooling, the mixture is filtered, the toluene phase is washed with water and dried over sodium sulfate, and the solvent is distilled off under reduced pressure (crude product: 14.5 g). Purification by column chromatography over silica gel using toluene as eluant gives 10.9 g of ester.

200 MHz NMR spectrum in CDCl$_3$: δ (ppm)=1.18–1.32 (12H); 1.8 and 2.01 (1H); 2.15 and 2.41 (1H); 3.24 (1H); 5.2 (2H); 6.13 and 6.93 (1H); 7.03–7.32 (3H).

MANUFACTURING EXAMPLE 6 a) 3-sec-Butyl-2-methyl-(α-ethynyl)-benzyl alcohol 50 ml of absolute THF is saturated under a nitrogen blanket at 0° C. with acetylene. While passing in further acetylene, 87 ml of methylmagnesium chloride solution (1.5 molar) is dripped in over a 45-minute period, and the whole is then stirred for 30 minutes at 0° C. At −20° C., a solution of 15.3 g of 3-sec-butyl-2-methylbenzaldehyde in 20 ml of absolute THF is dripped in. The mixture is stirred for 2 hours at −20° C., is allowed to stand overnight at room temperature, and is then poured into 300 ml of ice water. The mixture is acidified with dilute hydrochloric acid and extracted by shaking three times with ether. The combined ether extracts are washed with water, dried over sodium sulfate and concentrated. There is obtained 16.6 g of an oil (70% desired compound), which, after purification by column chromatography over silica gel using toluene as eluant, gives 5.1 g of the pure benzyl alcohol.

300 MHz NMR spectrum in CDCl$_3$: δ (ppm)=0.84 (3H); 1.17 (3H); 1.57 (2H); 2.36 (3H); 2.57 (1H); 2.62 (1H); 2.97 (1H); 5.62 (1H); 7.18 (2H); 7.52 (1H).

b) 2-Chloro-3-isopropyl-(α-ethynyl)-benzyl alcohol 30 ml of absolute THF is saturated under a nitrogen blanket at from 0°–10° C. with acetylene. While passing in further acetylene, 81.7 ml of vinylmagnesium chloride solution (1.47 molar) is dripped in and the mixture is stirred for 30 minutes at 0° C. Subsequently, 18.5 g of 2-chloro-3-isopropylbenzaldehyde is dripped in. The mixture is stirred for 15 hours at room temperature and then poured into 300 ml of ice water. The mixture is acidified with dilute hydrochloric acid and extracted by shaking three times with ether. The combined ether extracts are washed with water, dried and concentrated. There is obtained 22 g of crude product. Purification by column chromatography over silica gel with toluene-/acetone (95/%) as eluant gives 9 g of the desired compound.

300 MHz NMR spectrum in CDCl$_3$: δ (ppm)=1.23 (6H); 2.64 [1H+1H(OH)]; 3.47 (1H); 5.89 (1H); 7.3 (2H); 7.62 (1H).

MANUFACTURING EXAMPLE 7 cis,trans-3-(2'-chloro-3',3',3'-trifluoroprop-1'-enyl)-2,2-dimethylcyclopropane-1-carboxylic acid-[3-sec-butyl-2-methyl-(α-ethynyl)-benzyl]-ester At 20° C., 3.9 g of 3-(2'-chloro-3',3',3'-trifluoroprop-1'-enyl)-2,2-dimethylcyclopropane-1-carboxylic acid chloride is added dropwise to 2.85 g of 3-sec-butyl-2-methyl-(α-ethynyl)-benzyl alcohol and 1.4 g of 2-picoline in 20 ml of toluene. After the exothermic reaction has subsided the mixture is allowed to afterreact for 15 hours, is then filtered through silica gel and rinsed with toluene. After the solvent has been distilled off there remains 5.6 g of an oil.

Analysis: Calc. C, 64.7; H, 6.14; Cl, 8.3; F, 13.35. Found C, 65.3; H, 6.4; Cl, 7.8; F, 13.6.

300 MHz NMR spectrum in CDCl$_3$: δ (ppm)=0.84 (3H); 1.15-1.4 (9H); 1.6 (2H); 1.84; 2.06; 2.18 and partially masked signals (2H); 2.33 (3H); 2.63 (1H); 2.97 (1H); 5.87; 6.13 and 6.93 (1H); 6.62 (1H); 7.24 (2H); 7.51 (1H).

MANUFACTURING EXAMPLE 8 cis,trans-(2',2'-dichlorovinyl)-2,2-dimethylcyclopropane-1-carboxylic acid-(2-ethoxy-3-methylbenzyl)-ester a) Manufacture of the intermediates

Ethyl 2-ethoxy-3-methylbenzoate: at room temperature, a solution of 100.3 g of 2-hydroxy-3-methylbenzoic acid in 150 ml of DMF/THF (dimethylformamide/tetrahydrofuran, 1:1) is dripped into 43.6 g of sodium hydride (80% strength in white oil) in 350 ml of DMF/THF (1:1). The mixture is stirred for 40 minutes at 60° C. and then 226.5 g of ethyl iodide is dripped in at room temperature. After the addition of a further 250 ml of DMF/THF (1:1) the mixture is stirred for 9 hours at 60°-70° C. The reaction mixture is poured into ice water and extracted with ether. The combined organic phases are washed with water, dried and concentrated. There is obtained 126.3 g of the desired compound.

200 MHz NMR spectrum in CDCl$_3$: δ (ppm)=1.33-1.47 (6H); 2.31 (3H); 3.97 (2H); 4.37 (2H); 7.06 (1H); 7.34 (1H); 7.66 (1H).

2-Ethoxy-3-methylbenzyl alcohol: at 20°-25° C., a solution of 125.8 g of ethyl 2-ethoxy-3-methylbenzoate is dripped into 24.3 g of lithiumaluminum hydride in 500 ml of absolute THF. The mixture is stirred for 15 hours at room temperature, ice water is dripped in, and the mixture is acidified with concentrated hydrochloric acid and extracted with ether. The combined organic phases are washed with water, dried and concentrated. There is obtained 97.1 g of 2-ethoxy-3-methylbenzyl alcohol.

200 MHz NMR spectrum in CDCl$_3$: δ (ppm)=1.42 (3H); 2.29 (3H); 3.92 (2H); 4.72 (2H); 7.01 (1H); 7.12-7.23 (2H).

b) Manufacture of the benzyl ester

At room temperature, 8 g of 3-(2',2'-dichlorovinyl)-2,2-dimethylcyclopropane-1-carboxylic acid chloride is added dropwise to 5.8 g of 2-ethoxy-3-methylbenzyl alcohol and 4.5 g of triethylamine in 80 ml of toluene. After the exothermic reaction has subsided the mixture is stirred for 6 hours at 60° C. The toluene phase is filtered, washed several times with water, and dried, and the solvent is distilled off under reduced pressure. There is obtained 12.4 g of the desired benzyl ester.

Analysis: Calc. C, 60.5; H, 6.2; Cl, 19.9. Found C, 61.6; H, 6.6; Cl, 19.6.

300 MHz NMR spectrum in CDCl$_3$: δ (ppm)=1.16-1.46 (9H); 1.65; 1.89; 2.04 and partially masked signal (2H); 2.3 (3H); 3.89 (2H); 5.18 (2H); 5.6 and 6.3 (1H); 7.03 (1H); 7.2 (2H).

The esters according to the invention listed with physical properties in the table below were prepared by the above processes; the remaining compounds are readily obtainable by using appropriate starting materials.

TABLE

| No. | $A^{n*)}$ | $R^1$ | $R^2$ | $R^3$ | X | Physical data $^1$H-NMR: (MHz, LM) δ [ppm] melting point [°C.]. refractive index |
|---|---|---|---|---|---|---|
| 9 | $A^2$ | $CH_3$ | 1-Cyclopentenyl | H | H | |
| 10 | $A^{18}$ | $CH_3$ | 1-Cyclopentenyl | H | H | |
| 11 | $A^1$ | $CH_3$ | 1-Cyclohexenyl | H | 5-F | |
| 12 | $A^4$ | $C_2H_5$ | 1-Cyclohexenyl | H | H | |
| 13 | $A^2$ | $CH_3$ | 1-Cyclohexenyl | H | H | (200, CDCl$_3$)1.16-1.32(6H); 1.6-1.84(4H); 1.67-2.33(2H); 2.17(4H);2.26(3H); 5.13(2H); 5.56(1H); 5.63 and 6.3(1H); 7.05-7.3(3H) |
| 14 | $A^{12}$ | $CH_3$ | 1-Cyclohexenyl | H | H | |
| 15 | $A^{15}$ | $CH_3$ | 1-Cyclopentenyl | H | H | |
| 16 | $A^{20}$ | $CH_3$ | 1-cyclohexenyl | H | H | 81° C. |
| 17 | $A^{24}$ | $CH_3$ | 1-cycloheptenyl | H | H | |
| 18 | $A^4$ | $CH_3$ | 1-cyclohexenyl | H | H | (200, CDCl$_3$)1.17-1.32(6H); 1.73(4H); 1.95 and several masked signals(2H); 2.18(4H); 2.25(3H); 5.18(2H); 5.57(1H); 6.18 and 6.84(1H); 7.07-7.3(3H) |
| 19 | $A^2$ | $CH_3$ | 2-norbornen-2-yl | H | H | |
| 20 | $A^8$ | $CH_3$ | 2,5-norbornadien-2-yl | H | H | |
| 21 | $A^3$ | $CH_3$ | 2-norbornen-2-yl | H | H | |
| 22 | $A^4$ | $CH_3$ | 2-norbornen-2-yl | H | H | |
| 23 | $A^1$ | $CH_3$ | 2-norbornen-2-yl | H | H | |
| 24 | $A^8$ | $CH_3$ | 2-norbornen-2-yl | H | H | |
| 25 | $A^1$ | $CH_3$ | 1-cyclohexenyl | H | H | (200, CDCl$_3$)1.11-1.32(6H); 1.47 and 3 masked signals(2H); 1.72(6H+4H); 2.17(4H); 2.28(3H); 4.9 and 5.14(1H); 5.17(2H); 5.57(1H); 7.03-7.3(3H) |
| 26 | $A^{21}$ | $C_2H_5$ | 2-norbornen-2-yl | H | H | |
| 27 | $A^{18}$ | $C_2H_5$ | 2,5-norbornadien-2-yl | H | H | |
| 28 | $A^2$ | $CH_3$ | 2-norbornen-2-yl | H | 5-F | |
| 29 | $A^3$ | $CH_3$ | 1-cyclohexenyl | H | 5-Cl | |
| 30 | $A^4$ | $CH_3$ | 1-cyclopentenyl | H | 6-Cl | |
| 31 | $A^8$ | $CH_3$ | 1-cyclohexenyl | H | H | (200, CDCl$_3$)0.7(3H); 1.02(3H); 1.72(4H); 2.13(4H and |

TABLE-continued

| No. | A^(n*) | R^1 | R^2 | R^3 | X | Physical data  ^1H-NMR: (MHz, LM) δ [ppm]  melting point [°C]. refractive index |
|---|---|---|---|---|---|---|
| | | | | | | 3H); 2.32(1H); 3.2(1H); 5.11(2H); 5.52(1H); 7.03–7.15(3H); 7.28(4H) |
| 32 | A^21 | CH_3 | 2-norbornen-2-yl | H | H | |
| 33 | A^18 | CH_3 | 2-norbornen-2-yl | H | H | |
| 34 | A^2 | C_2H_5 | 1-cyclopentenyl | H | H | |
| 35 | A^3 | CH_3 | 2,5-norbornadien-2-yl | H | H | |
| 36 | A^3 | CH_3 | 1-cyclohexenyl | CN | H | (300, CDCl_3)1.2–1.41(6H); 1.74(4H); 1.85; 2.07; 2.48 and 1 masked signal(2H); 2.18(4H); 2.3(3H); 5.76(1H); 5.9; 6.17 and 6.87(1H); 6.76(1H); 7.14–7.27(2H); 7.5(1H) |
| 37 | A^2 | CH_3 | 1-cyclohexenyl | ethynyl | H | |
| 38 | A^4 | CH_3 | 1-cyclohexenyl | CH=CH_2 | H | |
| 39 | A^9 | CH_3 | 1-cyclohexenyl | ethynyl | H | |
| 40 | A^15 | CH_3 | 1-cyclopentenyl | CN | 5-F | |
| 41 | A^12 | CH_3 | 1-cyclohexenyl | CH_3 | H | |
| 42 | A^2 | CH_3 | 1-cyclohexenyl | CN | H | (200, CDCl_3)1.2–1.4(6H); 1.7(4H); 1.94 and 3 partially masked signals(2H); 2.2(4H); 2.33(3H); 5.58(1H); 5.63 and 6.23(1H); 6.6(1H); 7.19–7.33(2H); 7.53(1H) |
| 43 | A^1 | C_2H_5 | 1-cyclohexenyl | CN | H | |
| 44 | A^5 | C_2H_5 | 1-cyclohexenyl | ethynyl | H | |
| 45 | A^5 | CH_3 | 1-cyclohexenyl | ethyl | 5-Cl | |
| 46 | A^2 | CH_3 | 2-norbornen-2-yl | CN | H | |
| 47 | A2 | CH_3 | 2-norbornen-2-yl | ethynyl | H | |
| 48 | A^1 | CH_3 | 1-cyclohexenyl | CN | H | (200, CDCl_3)1.13–1.36(6H); 1.49 and 3 partially masked signals(2H); 1.73(6H and 4H); 2.19(4H); 2.32(3H); 4.91 and 5.32(1H); 5.57(1H); 6.58(1H); 7.15–7.31(2H); 7.53(1H) |
| 49 | A^2 | CH_3 | 2-norbornen-2-yl | CH=CH_2 | H | |
| 50 | A^2 | CH_3 | 2-norbornen-2-yl | CH_3 | H | |
| 51 | A^3 | CH_3 | 2-norbornen-2-yl | CN | H | |
| 52 | A^4 | CH_3 | 2-norbornen-2-yl | CN | H | |
| 53 | A^8 | CH_3 | 2-norbornen-2-yl | CN | H | |
| 54 | A^8 | CH_3 | 1-cyclohexenyl | CN | 5-Cl | |
| 55 | A^2 | CH_3 | 2,5-norbornadien-2-yl | CN | H | |
| 56 | A^2 | CH_3 | 2,5-norbornadien-2-yl | ethynyl | H | |
| 57 | A^3 | CH_3 | 2,5-norbornadien-2-yl | CN | H | |
| 58 | A^3 | CH_3 | 2,5-norbornadien-2-yl | ethynyl | H | |
| 59 | A^2 | CH_3 | 1,3-cyclohexdienyl | H | H | |
| 60 | A^3 trans | CH_3 | cyclohexyl | H | H | (200, CDCl_3)1.22–1.6(6H+5H); 1.75–1.99(5H). 2.36(3H); 2.49+masked signal(1H); 2.84(1H); 5.24(2H); 5.92 and 6.19(1H); 7.2–7.38(3H) |
| 61 | A^3 | CH_3 | 1,3-cyclohexadien-yl | H | H | |
| 62 | A^1 | CH_3 | cyclohexyl | H | H | |
| 63 | A^15 | CH_3 | cyclohexyl | H | H | |
| 64 | A^21 | CH_3 | cyclohexyl | H | 5-F | |
| 65 | A^3 cis | CH_3 | cyclohexyl | H | H | (300, CDCl_3)1.22–1.53(6H+5H); 1.74–1.92(5H); 2.02(1H); 2.16(1H); 2.3(3H); 3.78(1H); 5.15(2H); 6.65+6.97(1H); 7.12–7.27(3H) |
| 66 | A^18 | CH_3 | cyclohexyl | H | H | |
| 67 | A^2 | C_2H_5 | cyclohexyl | H | H | |
| 68 | A^2 | CH_3 | cyclopentyl | H | H | |
| 69 | A^3 | CH_3 | cyclopentyl | H | H | |
| 70 | A^3 | CH_3 | cycloheptyl | H | H | |
| 71 | A^2 | CH_3 | cyclohexyl | H | H | (200, CDCl_3)1.14–1.5(6H and 5H); 1.67; 2.02 and 2 partially masked signals(2H); 1.84(5H); 2.31(3H); 2.8(1H); 5.18(2H); 5.63 and 6.33(1H); 7.2–7.33(3H) |
| 72 | A^2 | CH_3 | norborn-2-yl | H | H | 1.07–2.08(15H); 2.27(1+2H); 2.25(3H); 3.46(1H); 5.12(2H); 5.61 and 6.3(1H); 7.18(2H); 7.27(1H) |
| 73 | A^3 | CH_3 | norborn-2-yl | H | H | 1.18–2.22(15H); 2.25–2.48(1H+2H+3H); 3.45(1H); 5.17(2H); 5.87, 6.13, 6.65 and 6.96(1H); 7.15–7.32(3H) |
| 74 | A^4 | CH_3 | norborn-2-yl | H | H | |
| 75 | A^8 | CH_3 | norborn-2-yl | H | H | (300, CDCl_3); 0.69(3H); 1.01(3H); 1.17–1.66(7H); 1.88(1H); 2.14(3H); 2.25–2.4(3H); 3.18(1H); 3.42(1H); 5.0–5.2(2H); 7.06–7.33(7H) |
| 76 | A^18 | CH_3 | norborn-2-yl | H | H | (200, CDCl_3); 0.95–1.1(6H); 1.15–1.7(7H); 1.92(1H); 2.28–2.41(3H+3H); 3.45(1H); 3.99(1H); 5.14(1H); 5.22(2H); 6.63(1H); 7.15–7.39(4H); 7.55(1H) |
| 77 | A^4 | CH_3 | cyclohexyl | H | H | (300, CDCl_3)1.18–1.54(6H and 5H); 1.7; 2.22 and 2 2 masked signals(2H); 1.73–1.97(5H); 2.31(3H); 2.8(1H); 5.16(2H); 6.16 and 6.82(1H); 7.15–7.28(3H) |
| 78 | A^21 | CH_3 | norborn-2-yl | H | H | n_D^{22}: 1.5427 |
| 79 | A^2 | CH_3 | cyclopropyl | H | H | (200, CDCl_3); 0.65(2H); 0.95(2H); 1.18–1.34(6H); 1.92(1H); 1.68; 1.92, 2.06 and 2.32(2H); 2.44(3H); 5.2(2H); 5.63 and 6.32(1H); 7.05–7.28(3H) |
| 80 | A^1 | CH_3 | cyclopropyl | H | H | |
| 81 | A^3 | CH_3 | cyclopropyl | H | H | (200, CDCl_3); 0.67(2H); 0.96(2H); 1.22–1.4(6H); 1.94(1H); 1.86; 2.08; 2.22 and 2.38(2H); 2.47(3H); 5.23(2H); 6.19 and 7.02(1H, 7.06–7.3(3H) |
| 82 | A^4 | CH_3 | cyclopropyl | H | H | |

TABLE-continued

| No. | A[n*] | R[1] | R[2] | R[3] | X | Physical data $^1$H-NMR: (MHz, LM) δ [ppm] melting point [°C], refractive index |
|---|---|---|---|---|---|---|
| 83 | A[8] | CH$_3$ | cyclohexyl | H | H | (200, CDCl$_3$)0.68(3H); 1.1(3H); 1.4(5H); 1.8(5H); 2.14(3H); 2.32(1H); 2.74(1H); 3.18(1H); 5.12(2H); 7.1–7.34(7H) |
| 84 | A[8] | CH$_3$ | cyclopropyl | H | H | (200, CDCl$_3$); 0.6(2H); 0.71(3H); 0.93(2H); 1.04(3H); 1.88(1H); 2.22–2.43(1H); 2.31(3H); 3.21(1H); 5.15(2H); 7.11(3H); 7.3(4H) |
| 85 | A[15] | CH$_3$ | cyclopropyl | H | H | |
| 86 | A[18] | CH$_3$ | cyclopropyl | H | H | |
| 87 | A[21] | CH$_3$ | cyclopropyl | H | H | |
| 88 | A[20] | CH$_3$ | cyclopropyl | H | H | |
| 89 | A[3] | CH$_3$ | cyclohexyl | CN | H | (200, CDCl$_3$)1.18–1.53(6H+5H); 1.71–1.93(5H); 2.35(3H); 2.02; 2.22; 2.44 and 1 masked signal(2H); 2.78(1H); 6.13 and 6.86(1H); 6.56(1H); 7.17–7.49(3H) |
| 90 | A[2] | CH$_3$ | cyclopropyl | CN | H | |
| 91 | A[4] | CH$_3$ | cyclopropyl | ethynyl | H | |
| 92 | A[3] | CH$_3$ | cyclohexyl | ethynyl | H | |
| 93 | A[8] | CH$_3$ | cyclohexyl | CH$_3$ | H | |
| 94 | A[18] | CH$_3$ | cyclohexyl | CH=CH$_2$ | H | |
| 95 | A[4] | CH$_3$ | cyclohexyl | CN | H | (200, CDCl$_3$)1.13–1.6(6H+5H); 1.63–1.92(5H); 2.01 and 3 partially masked signals(2H); 2.33(3H); 2.76 (1H); 6.15 and 6.70(1H); 6.55(1H); 7.2–7.48(3H) |
| 96 | A[1] | CH$_3$ | norborn-2-yl | CN | H | |
| 97 | A[2] | CH$_3$ | norborn-2-yl | CN | H | |
| 98 | A[3] | CH$_3$ | norborn-2-yl | ethynyl | H | |
| 99 | A[4] | CH$_3$ | norborn-2-yl | isopropyl | H | |
| 100 | A[18] | CH$_3$ | norborn-2-yl | CN | 5-F | |
| 101 | A[2] | CH$_3$ | cyclohexyl | CN | H | (300, CDCl$_3$); 1.16–1.48(6H+5H); 1.67; 2.12 and 2 partially masked signals(2H); 1.73–1.96(5H); 2.38(3H); 2.78(1H); 5.62 and 6.2(1H); 6.58(1H); 7.14–7.47(3H); |
| 102 | A[2] | CH$_3$ | (norborn-2-yl structure) | H | H | |
| 103 | A[4] | CH$_3$ | (norborn-2-yl structure) | CN | H | |
| 104 | A[8] | CH$_3$ | (norborn-2-yl structure) | ethynyl | H | |
| 105 | A[2] | CH$_3$ | cyclopentyl | CN | H | |
| 106 | A[4] | C$_2$H$_5$ | cycloheptyl | CN | H | |
| 107 | A[2] | CH$_3$ | isopropyl | H | H | (300, CDCl$_3$); 1.16–1.34(12H); 1.66; 1.9; 2.04 and 2.25–2.36(2H); 2.31(3H); 3.23(1H); 5.16(2H); 5.61 and 6.3(1H); 7.14–7.31(3H) |
| 108 | A[8] | CH$_3$ | isopropyl | H | H | |
| 109 | A[15] | CH$_3$ | isopropyl | H | H | (250, CDCl$_3$); 1.21(9H); 1.35(3H); 1.73(1H); 2.3(3H); 2.57(1H); 3.22(1H); 5.18(2H); 5.83(1H); 7.18(2H); 7.27(3H); 7.44(2H) |
| 110 | A[18] | CH$_3$ | isopropyl | H | H | (200, CDCl$_3$); 0.99(6H); 1.21(6H); 2.24(3H); 3.22(1H); 4.0(1H); 5.13(1H); 5.25(2H); 6.62(1H); 7.17–7.4(4H); 7.55(1H) |
| 111 | A[19] | CH$_3$ | isopropyl | H | H | |
| 112 | A[20] | CH$_3$ | isopropyl | H | H | 51–56° C. |
| 113 | A[1] | CH$_3$ | isopropyl | H | H | (300, CDCl$_3$); 1.07–1.3(12H); 1.46; 1.88; 2.09 and 1 masked signal(2H); 1,71(6H); 2.33(3H); 3.22(1H); 4.89 and 5.4(1H); 5.12(2H); 7.11–7.28(3H) |
| 114 | A[21] | CH$_3$ | isopropyl | H | H | n$_D^{22}$: 1.5190 |
| 115 | A[22] | CH$_3$ | isopropyl | H | H | |
| 116 | A[24] | CH$_3$ | isopropyl | H | H | |
| 117 | A[2] | C$_2$H$_5$ | isopropyl | H | H | |
| 118 | A[4] | CH$_3$ | isopropyl | H | 5-F | |
| 119 | A[4] | CH$_3$ | isopropyl | H | H | (200, CDCl$_3$); 1.19–1.35(12H); 1.72; 1.9–2.05 and 2.25(2H); 2.33(3H); 3.26(1H); 5.2(2H); 6.2 and 6.87(1H); 7.21–7.38(3H) |
| 120 | A[2] | CH$_3$ | isopropyl | H | 6-Cl | |

TABLE-continued

| No. | A$^{n*}$) | R$^1$ | R$^2$ | R$^3$ | X | Physical data $^1$H-NMR: (MHz, LM) δ [ppm] melting point [°C]. refractive index |
|---|---|---|---|---|---|---|
| 121 | A$^3$ | CH$_3$ | —CH(C$_2$H$_5$)$_2$ | H | H | (200, CDCl$_3$); 0.74(6H); 1.18–1.34(6H); 1.47–1.77(4H); 1.82; 2.03; 2.16 and 2.43(2H); 2.82(1H); 5.18(2H); 6.14 and 6.96(1H); 7.17(3H) |
| 122 | A$^2$ | CH$_3$ | —CH(C$_2$H$_5$)$_2$ | H | H | (200, CDCl$_3$); 0.78(6H); 1.15–1.3(6H); 1.44–1.76(4H); 1.9; 2.02 and two partially masked signals(2H); 2.27(3H); 2.82(1H); 5.17(2H); 5.62 and 6.3(1H); 7.17(3H) |
| 123 | A$^1$ | CH$_3$ | —CH(C$_2$H$_5$)$_2$ | H | H | |
| 124 | A$^2$ | CH$_3$ | —CH(CH$_3$)(n-C$_3$H$_7$) | H | H | |
| 125 | A$^2$ cis | CH$_3$ | sec-Butyl | H | H | (300, CDCl$_3$); 0.86(3H); 1.18–1.29(9H)1.6(2H); 1.9(1H); 2.03(1H); 2.29(3H); 2.97(1H); 5.13(2H); 6.3(1H); 7.13–7.25(3H) |
| 126 | A$^3$ | CH$_3$ | —CH(CH$_3$)(n-C$_3$H$_7$) | H | H | |
| 127 | A$^{21}$ | CH$_3$ | —CH(CH$_3$)(n-C$_3$H$_7$) | H | H | |
| 128 | A$^8$ | CH$_3$ | —CH(C$_2$H$_5$)$_2$ | H | H | |
| 129 | A$^4$ | CH$_3$ | —CH(C$_2$H$_5$)(n-C$_4$H$_9$) | H | H | |
| 130 | A$^2$ | CH$_3$ | —CH(C$_2$H$_5$)(n-C$_4$H$_9$) | H | H | |
| 131 | A$^2$ trans | CH$_3$ | sec-butyl | H | H | (300. CDCl$_3$); 0.86(3H); 1.16–1.31(9H); 1.52–1.7(2H+1H); 2.23–2.37(1H and 3H); 2.96(1H); 5.17(2H); 5.6(1H); 7.14–7.26(3H); |
| 132 | A$^2$ | CH$_3$ | —CH(CH$_3$)(i-C$_3$H$_7$) | H | H | |
| 133 | A$^4$ | CH$_3$ | —CH(C$_2$H$_5$)(i-C$_3$H$_7$) | H | H | |
| 134 | A$^8$ | CH$_3$ | —CH(i-C$_3$H$_7$)$_2$ | H | H | |
| 135 | A$^{15}$ | CH$_3$ | n-butyl | H | H | |
| 136 | A$^3$ | CH$_3$ | n-propyl | H | H | |
| 137 | A$^3$ cis | CH$_3$ | sec-butyl | H | H | (300, CDCl$_3$); 0.88(3H); 1.2(3H); 1.28(6H); 1.61(2H); 2.03(1H); 2.16(1H); 2.3(3H); 2.96(1H); 5.16(2H); 6.97(1H); 7.13–7.24(3H); |
| 138 | A$^2$ | CH$_3$ | —CH(CH$_3$)(i-C$_3$H$_7$) | CN | H | |
| 139 | A$^4$ | CH$_3$ | —CH(i-C$_3$H$_7$)$_2$ | ethynyl | H | |
| 140 | A$^8$ | CH$_3$ | —CH(C$_2$H$_5$)$_2$ | —CH=CH$_2$ | H | |

TABLE-continued

| No. | A[n*] | R[1] | R[2] | R[3] | X | Physical data<br>$^1$H-NMR: (MHz, LM) δ [ppm]<br>melting point [°C], refractive index |
|---|---|---|---|---|---|---|
| 141 | A[18] | $CH_3$ | 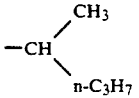 | —$CH_3$ | H | |
| 142 | A[2] | $CH_3$ | n-propyl | H | H | |
| 143 | A[3] trans | $CH_3$ | sec-butyl | H | H | (300, $CDCl_3$)0.85(3H); 1.17–1.38(3H+6H); 1.61(2H); 1.82(1H); 2.29(3H); 2.43(1H); 2.97(1H); 5.18(2H); 5.87 and 6.15(1H); 7.14–7.25(3H) |
| 144 | A[2] | $CH_3$ | 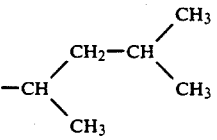 | H | H | |
| 145 | A[4] | $CH_3$ | 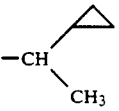 | H | H | |
| 146 | A[18] | $CH_3$ | 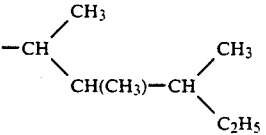 | H | H | |
| 147 | A[21] | $CH_3$ | 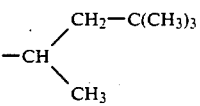 | H | H | |
| 148 | A[8] | $CH_3$ | 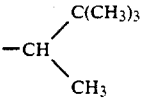 | H | H | |
| 149 | A[8] | $CH_3$ | sec-butyl | H | H | (300, $CDCl_3$)0.68(3H); 0.82(3H); 1.01(3H); 1.18(3H); 1.59(2H); 2.12(3H); 2.25–2.38(1H); 2.92(1H); 3.17(1H); 5.02–5.18(2H); 7.06–7.28(3H+4H) |
| 150 | A[2] | $CH_3$ | cyclopropyl | ethynyl | H | |
| 151 | A[4] | $CH_3$ | cyclopropyl | H | H | |
| 152 | A[3] | $CH_3$ | cyclopropyl | isopropyl | H | |
| 153 | A[12] | $CH_3$ | 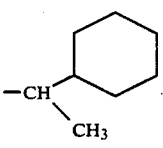 | H | H | |
| 154 | A[21] | $CH_3$ | sec-butyl | CN | H | |
| 155 | A[21] | $CH_3$ | sec-butyl | H | H | (300, $CDCl_3$)0.66–1.0(9H); 1.18(3H); 1.57(2H); 2.18(3H); 2.33–2.5(1H); 2.94(1H); 4.13(1H); 5.1–5.25(2H); 6.15(2H); 6.75(2H); 7.07–7.23(3H) |
| 156 | A[2] | $CH_3$ | sec-Butyl | CN | H | |
| 157 | A[21] | $CH_3$ | isopropyl | isopropyl | H | |
| 158 | A[18] | $CH_3$ | isopropyl | $CH=CH_2$ | 5-F | |
| 159 | A[4] | $CH_3$ | isopropyl | ethyl | H | |
| 160 | A[2] | $CH_3$ | isopropyl | CN | H | |
| 161 | A[3] | $CH_3$ | sopropyl | CN | H | (300, $CDCl_3$)1.18–1.42(6H+6H); 1.75–1.9; 2.07 and partially masked signals(2H); 2.37(3H); 3.22(1H); 6.1–6.22 and 6.81–6.92(1H); 7.22–7.47(3H) |
| 162 | A[2] | $CH_3$ | isopropyl | ethynyl | H | |
| 163 | A[10] | $CH_3$ | 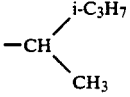 | $CH_3$ | 5-Cl | |

TABLE-continued

| No. | A[n*] | R[1] | R[2] | R[3] | X | Physical data $^1$H-NMR: (MHz, LM) δ [ppm] melting point [°C], refractive index |
|---|---|---|---|---|---|---|
| 164 | A[15] | CH$_3$ | n-butyl | CH=CH$_2$ | H | |
| 165 | A[2] | CH$_3$ | sec-butyl | CN | H | |
| 166 | A[3] | CH$_3$ | sec-butyl | CN | H | |
| 167 | A[2] | CH$_3$ | sec-butyl | ethynyl | H | (300, CDCl$_3$)0.87(3H); 1.15–1.37(9H); 1.5–1.7(2H); 1.91; 2.03 and 2 partially masked signals(2H); 2.3(3H); 2.64(1H); 2.98(1H); 5.6 and 6.22–6.31(1H); 6.58–6.66(1H), 7.22(2H); 7.52(1H) |
| 168 | A[4] | CH$_3$ | sec-butyl | CH=CH$_2$ | H | |
| 169 | A[21] | CH$_3$ | isopropenyl | ethyl | H | |
| 170 | A[18] | CH$_3$ | isopropenyl | CN | H | |
| 171 | A[8] | CH$_3$ | isopropenyl | H | 5-F | |
| 172 | A[4] | CH$_3$ | isopropenyl | H | H | |
| 173 | A[3] cis | CH$_3$ | isopropenyl | H | H | (300, CDCl$_3$)1.29(6H); 2.0–2.08(3H and 1H); 2.19(1H); 2.30(3H); 4.84(1H); 5.16(2H); 5.23(1H); 6.97(1H); 7.1–7.27(3H); |
| 174 | A[2] | CH$_3$ | isopropenyl | CN | H | |
| 175 | A[2] | CH$_3$ | isopropenyl | ethynyl | H | |
| 176 | A[2] | CH$_3$ | $\begin{array}{c}\text{CH}_3\\|\\-\text{C}=\text{CH}-\text{CH}_3\end{array}$ | H | H | |
| 177 | A[3] | CH$_3$ | $\begin{array}{c}\text{C}_2\text{H}_5\\|\\-\text{C}=\text{CH}_2\end{array}$ | H | H | |
| 178 | A[2] | C$_2$H$_5$ | isopropenyl | H | H | |
| 179 | A[3] trans | CH$_3$ | isopropenyl | H | H | (300, CDCl$_3$)1.22(3H); 1.34(3H); 1.83(1H); 2.03(3H); 2.3(3H); 2.45(1H); 4.84(1H); 5.19(2H); 5.22(1H); 6.15(1H); 7.1–7.27(3H); |
| 180 | A[4] | CH$_3$ | $\begin{array}{c}\text{C}_2\text{H}_5\\|\\-\text{C}=\text{CH}-\text{CH}_3\end{array}$ | H | H | |
| 181 | A[2] | CH$_3$ | $\begin{array}{c}\text{C}_2\text{H}_5\\|\\-\text{C}=\text{CH}_2\end{array}$ | H | H | |
| 182 | A[2] | CH$_3$ | $\begin{array}{c}\text{C}_2\text{H}_5\\|\\-\text{C}=\text{CH}-\text{CH}_3\end{array}$ | H | H | (300, CDCl$_3$); 0.88 and 0.98(3H); 1.15–1.30(6H); 1.33 and 1.78(3H); 1.66; 1.91; 2.04 and 1 masked signal (2H); 2.14–2.41(3H+2H); 5.13(2H); 5.29 and 5.6(1H); 5.62 and 6.3(1H); 6.97–7.26(3H) |
| 183 | A[8] | CH$_3$ | $\begin{array}{c}\text{i-C}_3\text{H}_7\\|\\-\text{C}=\text{CH}_2\end{array}$ | H | H | |
| 184 | A[2] | CH$_3$ | $\begin{array}{c}\text{n-C}_3\text{H}_7\\|\\-\text{C}=\text{CH}-\text{C}_2\text{H}_5\end{array}$ | H | H | |
| 185 | A[15] | CH$_3$ | $\begin{array}{c}\text{n-C}_3\text{H}_7\\|\\-\text{C}=\text{CH}_2\end{array}$ | H | H | |
| 186 | A[2] | CH$_3$ | $\begin{array}{c}\text{CH}_3\\|\\-\text{C}=\text{CH}-\text{CH}_3\end{array}$ | ethynyl | H | |
| 187 | A[8] | CH$_3$ | 1-cyclohexenyl | CN | H | (200, CDCl$_3$)0.68–1.18(6H); 1.72(4H); 2.02–2.22(3H and 4H); 2.37(1H); 3.24(1H); 5.5(1H); 6.46(1H); 7.13–7.49(7H); |
| 188 | A[20] | CH$_3$ | $\begin{array}{c}\text{CH}_2-\text{CH}_2-\text{CH}=\text{CH}_2\\|\\-\text{C}=\text{CH}_2\end{array}$ | H | H | |
| 189 | A[2] | CH$_3$ | vinyl | H | H | (300, CDCl$_3$); 1.15–1.3(6H); 1.63; 1.88; 2.03 and one partially masked signal(2H); 2.32(3H); 5.13(2H); 5.32(1H); 5.6(1H); 5.6 and 6.28(1H); 6.94–7.05(1H); 7.13–7.3(2H); 7.45(1H) |
| 190 | A[3] | CH$_3$ | $\begin{array}{c}\text{C}_2\text{H}_5\\|\\-\text{C}=\text{CH}-\text{CH}_3\end{array}$ | CN | H | |
| 191 | A[2] | CH$_3$ | $\begin{array}{c}\text{n-C}_3\text{H}_7\\|\\-\text{C}=\text{CH}-\text{C}_2\text{H}_5\end{array}$ | H | H | |

TABLE-continued

| No. | A[n*] | R[1] | R[2] | R[3] | X | Physical data<br>$^1$H-NMR: (MHz, LM) δ [ppm]<br>melting point [°C], refractive index |
|---|---|---|---|---|---|---|
| 192 | A[21] | $CH_3$ | $-\underset{\underset{CH_3}{|}}{C}=CH-(i-C_3H_7)$ | H | H | |
| 193 | A[3] | $CH_3$ | 1-cyclohexenyl | H | H | (200, CDCl$_3$)1.2-1.36(6H); 1.76(4H); 1.85; 2.05;<br>masked signal and 2.46(2H); 2.18(4H); 2.27(3H);<br>5.18(2H); 5.57(1H); 5.91; 6.16 and 6.97(1H);<br>7.07-7.3(3H); |
| 194 | A[8] | $CH_3$ | $-\underset{\underset{CH_2-CH(CH_3)_2}{|}}{C}=CH_2$ | H | H | |
| 195 | A[24] | $CH_3$ |  | ethynyl | H | |
| 196 | A[3] | $CH_3$ | $-\underset{\underset{CH_3}{|}}{C}=CH-CH_3$ | H | H | |
| 197 | A[4] | $CH_3$ | $-\underset{\underset{C_2H_5}{|}}{C}=CH-CH_3$ | CN | H | |
| 198 | A[3] | $CH_3$ | vinyl | H | H | n$_D$[22]: 1.5065 |
| 199 | A[2] | $CH_3$ | $-CH=CH-CH_3$ | H | H | |
| 200 | A[3] | $CH_3$ | $-CH=CH-CH(CH_3)_2$ | H | H | |
| 201 | A[4] | $CH_3$ | $-CH=C(CH_3)_2$ | H | H | |
| 202 | A[18] | $CH_3$ | $-\underset{\underset{CH_3}{|}}{C}=C(CH_3)_2$ | H | H | |
| 203 | A[21] | Cl | isopropyl | H | H | (300, CDCl$_3$); 0.75(3H); 0.99(3H); 1.23(6H); 2.45(1H);<br>3.46(1H); 4.2(1H); 5.27(2H); 6.17(2H); 6.8(2H);<br>7.07-7.32(3H) |
| 204 | A[2] | Cl | isopropyl | H | H | (300, CDCl$_3$)1.15-1.36(12H); 1.7; 1.93; 2.05 and<br>2.29(2H); 3.46(1H); 5.23(2H); 5.62 and 6.3(1H);<br>7.2-7.31(3H) |
| 205 | A[4] | Cl | isopropyl | H | H | |
| 206 | A[10] | Cl | isopropyl | H | H | |
| 207 | A[15] | Cl | isopropyl | H | H | (250, CDCl$_3$); 1.22(9H); 1.37(3H); 1.78(1H); 2.57(1H);<br>3.45(1H); 5.3(2H); 5.85(1H); 7.26(2H+3H); 7.44(2H) |
| 208 | A[18] | Cl | isopropyl | H | H | (300, CDCl$_3$); 1.0-1.08(6H); 1.25(6H); 2.28(1H);<br>3.47(1H); 4.0(1H); 5.11(1H); 5.29(2H); 6.63(1H);<br>7.17-7.33(4H); 7.52(1H) |
| 209 | A[20] | Cl | isopropyl | H | H | |
| 210 | A[3] | Cl | isopropyl | H | H | (300, CDCl$_3$)1.2-1.36(12H); 1.87; 2.08; 2.2 and<br>2.47(2H); 3.47(1H); 5.26(2H); 6.17 and 6.97(1H);<br>7.23-7.32(3H) |
| 211 | A[24] | Cl | isopropyl | H | H | |
| 212 | A[19] | Cl | isopropyl | H | H | |
| 213 | A[23] | Cl | isopropyl | H | H | |
| 214 | A[2] | Cl | tert.-butyl | H | H | (300, CDCl$_3$); 1.19-1.32(6H); 1.52(9H); 1.71; 1.95;<br>2.07 and 2.3(2H); 5.27(2H); 5.62 and 6.3(1H);<br>7.18-7.3(2H); 7.42(1H) |
| 215 | A[3] | Cl | tert-butyl | H | H | |
| 216 | A[1] | Cl | isopropyl | H | H | (300, CDCl$_3$)1.11-1.32(6H); 1.5; 1.93; 2.11<br>and 1 partially masked signal(2H); 1.72(6H);<br>3.47(1H); 4.92 und 5.4(1H); 5.25(2H); 7.26(3H) |
| 217 | A[2] | Cl | isopropyl | H | 5-Cl | |
| 218 | A[3] | Cl | isopropyl | H | 6-Cl | |
| 219 | A[15] | Cl | tert-butyl | H | H | |
| 220 | A[21] | Cl | tert.-butyl | H | H | (200, CDCl$_3$); 0.76(3H); 0.99(3H); 1.5(9H); 2.46(1H);<br>4.21(1H); 5.3(2H); 6.18(2H); 6.82(2H); 7.17(2H);<br>7.43(1H) |
| 221 | A[20] | Cl | sec-butyl | H | H | |
| 222 | A[2] | Cl | $-CH(C_2H_5)_2$ | H | H | |
| 223 | A[8] | Cl | isopropyl | H | H | (300, CDCl$_3$)0.7(3H); 1.03(3H); 1.22(6H); 2.33(1H);<br>3.22(1H); 3.44(1H); 5.12-5.3(2H); 7.03-7.32(3H+4H) |
| 224 | A[2] | Cl | isopropyl | H | 6-Cl | |
| 225 | A3 | Cl | ethyl | H | H | (300, CDCl$_3$); 1.2-1.38(6H+3H); 1.78; 1.86; 1.98; 2.07;<br>2.19 and 2.46(2H); 2.8(2H); 5.25(2H); 5.88; 6.16; 6.64<br>and 6.95(1H); 7.24(3H) |
| 226 | A[2] | Cl | ethyl | H | H | |
| 227 | A[21] | Cl | ethyl | H | H | |

TABLE-continued

| No. | A[n*] | R[1] | R[2] | R[3] | X | Physical data<br>$^1$H-NMR: (MHz, LM) δ [ppm]<br>melting point [°C], refractive index |
|---|---|---|---|---|---|---|
| 228 | A[24] | Cl | ethyl | H | H | |
| 229 | A[2] | Cl | cyclopentyl | H | H | |
| 230 | A[3] | Cl | cyclopentyl | H | H | (300, CDCl3); 1.2-1.38(6H); 1.45-2.5(8H+2H); 3.49(1H); 5.26(2H); 5.89; 6.17; 6.64 and 6.95(1H); 7.12-7.33(3H) |
| 231 | A[2] | Cl | isopropyl | ethynyl | H | (200, CDCl3)1.15-1.34(12H); 1.68; 1.93; 2.05 and 2.22-2.37(2H); 2.68(1H); 3.49(1H); 5.63 and 6.3(1H); 6.82(1H); 7.38(2H); 7.7(1H); |
| 232 | A[2] | Cl | sec.-butyl | H | H | (200, CDCl3); 0.82(3H); 1.15-1.3(9H); 1.5-2.32(4H); 3.27(1H); 5.24(2H); 5.61 and 6.29(1H); 7.25(3H) |
| 233 | A[3] | Cl | sec.-butyl | H | H | (200, CDCl3); 0.82(3H); 1.17-1.38(9H); 1.6(2H); 1.96; 2.07; 2.19 and 2.45(2H); 3.28(1H); 5.25(2H); 6.16 and 6.94(1H); 7.23(3H) |
| 234 | A[2] | Cl | cyclopentyl | CN | H | |
| 235 | A[3] | Cl | ethyl | ethynyl | H | |
| 236 | A[21] | Cl | cyclopentyl | H | H | (300, CDCl3); 0.73(3H); 0.98(3H); 1.55(2H); 1.75(4H); 2.08(2H); 2.45(1H); 3.48(1H); 4.2(1H); 5.25(2H); 6.15(2H); 6.78(2H); 7.04-7.3(3H) |
| 237 | A[2] | Cl | cycloheptyl | H | H | |
| 238 | A[3] | Cl | cyclohexyl | H | H | (200, CDCl3); 1.31-1.62(6H+6H); 1.83-2.63(4H+2H); 3.2(1H); 5.38(2H); 6.01; 6.28; 6.77 and 7.07(1H); 7.38(3H) |
| 239 | A[3] | Cl | isopropyl | ethynyl | H | (300, CDCl3)1.16-1.38(12H); 1.75-1.85; 2.02; 2.2 and 2.47(2H); 2.66(1H); 3.46(1H); 5.84; 6.14 and 6.93(1H); 7.33(2H); 7.65(1H) |
| 240 | A[19] | Cl | cyclohexyl | ethynyl | H | |
| 241 | A[2] | Cl | cyclohexyl | H | H | (200, CDCl3); 1.21-2.41(10H+6H+2H); 3.1(1H); 5.28(2H); 5.65 and 6.31(1H); 7.3(3H) |
| 242 | A[21] | Cl | cyclohexyl | H | H | |
| 243 | A[2] | Cl | cyclohexyl | CN | H | |
| 244 | A[21] | Cl | isopropyl | ethynyl | H | |
| 245 | A[2] | Cl | cyclopropyl | H | H | |
| 246 | A[3] | Cl | isopropyl | CN | H | |
| 247 | A[2] | Cl | isopropyl | CN | H | (200, CDCl3)1.2-1.38(6H and 6H); 1.72; 1.96; 2.16 and 2.33(2H); 3.5(1H); 5.66 and 6.17-6.31(1H); 6.8(1H); 7.34-7.51(2H); 7.62(1H) |
| 248 | A[3] | Cl | cyclopropyl | H | H | |
| 249 | A[21] | Cl | cyclopropyl | H | H | |
| 250 | A[21] | F | isopropyl | H | H | (300, CDCl3); 0.74(3H); 0.95(3H); 1.25(6H); 2.42(1H); 3.23(1H); 4.18(1H); 5.2(2H); 6.15(2H); 6.79(2H); 7.06(2H); 7.23(1H) |
| 251 | A[2] | F | tert.-butyl | H | H | (200, CDCl3); 1.18-1.31(6H); 1.41(9H); 1.68; 1.9; 2.05 and 2.28(2H); 5.22(2H); 5.62 and 6.3(1H); 7.09(1H); 7.3(2H) |
| 252 | A[3] | F | cyclopentyl | H | H | |
| 253 | A[2] | F | cyclopropyl | H | H | |
| 254 | A[21] | F | cyclohexyl | H | H | |
| 255 | A[2] | F | ethyl | H | H | |
| 256 | A[2] | F | isopropyl | CN | H | (300, CDCl3); 1.18-1.38(12H); 1.69; 1.91; 2.12 and 2.32(2H); 3.28(1H); 5.62 and 6.2(1H); 6.63(1H); 7.2(1H); 7.35-7.5(2H) |
| 257 | A[2] | F | isopropyl | H | H | (200, CDCl3)1.14-1.31(12H); 1.67; 1.88; 2.04 and 2.26(2H); 3.27(1H); 5.2(2H); 5.62 and 6.3(1H); 7.05-7.32(3H) |
| 258 | A[2] | F | methyl | H | H | |
| 259 | A[2] | Cl | methyl | H | H | |
| 260 | A[2] | F | sec-butyl | H | H | |
| 261 | A[2] | F | cyclopentyl | H | H | |
| 262 | A[3] | F | tert-butyl | H | H | |
| 263 | A[3] | F | cyclopropyl | H | H | |
| 264 | A[3] | F | cyclohexyl | H | H | |
| 265 | A[21] | F | ethyl | H | H | |
| 266 | A[21] | F | cyclopropyl | H | H | |
| 267 | A[2] | F | —CH(C2H5)2 | isopropyl | H | |
| 268 | A[3] trans | Cl | isopropyl | H | H | (300, CDCl3)1.19-1.38(12H); 1.87(1H); 2.47(1H); 3.47(1H); 5.27(2H); 6.17(1H); 7.26(3H); |
| 269 | A[3] | Cl | norborn-2-yl | H | H | |
| 270 | A[2] | F | norborn-2-yl | H | H | |
| 271 | A[2] | Cl | CH3<br>\|<br>—C=CH—CH3 | H | H | |
| 272 | A[21] | F | CH3<br>\|<br>—C=CH—CH3 | H | H | |
| 273 | A[2] | Cl | 2-cyclohexenyl | H | H | |
| 274 | A[15] | F | 1-cyclohexenyl | H | H | |
| 275 | A[3] | F | norborn-2-yl | H | H | |

TABLE-continued

| No. | A[n*] | R[1] | R[2] | R[3] | X | Physical data $^1$H-NMR: (MHz, LM) δ [ppm] melting point [°C], refractive index |
|---|---|---|---|---|---|---|
| 276 | A[2] | Cl | norborn-2-yl | H | H | |
| 277 | A[21] | Cl | norborn-2-yl | H | H | |
| 278 | A[2] | Cl | 2-cyclopentenyl | H | H | |
| 279 | A[2] | OC$_2$H$_5$ | cyclohexyl | H | H | (300, CDCl$_3$)1.14–1.53(14H); 1.65; 2.03; 2.23–2.35 and a partially masked signal(2H); 1.7–1.93(5H); 2.92(1H); 3.77–3.94(2H); 5.19(2H); 5.61 and 6.31(1H); 7.03–7.28(3H) |
| 280 | A[3] | Cl | −CH(CH$_3$)CH=CH$_2$ | H | H | |
| 281 | A[2] | F | −CH(CH$_3$)CH=CH$_2$ | H | H | |
| 282 | A[3] | Cl | −C(CH$_3$)=CH−CH$_3$ | H | H | |
| 283 | A[2] | F | −C(CH$_3$)=CH−CH$_3$ | H | H | |
| 284 | A[21] | Cl | cyclohexyl | H | 5-Cl | |
| 285 | A[4] | Cl | 2-cyclopentenyl | H | H | |
| 286 | A[2] | Br | isopropyl | H | H | (300, CDCl$_3$); 1.17–1.31(12H); 1.7; 2.95; 2.07 and 2.29(2H); 3.46(1H); 5.23(2H); 5.62 and 6.3(1H); 7.27(3H); |
| 287 | A[3] | Br | isopropyl | H | H | (300, CDCl$_3$); 1.2–1.37(12H); 1.8; 1.87; 2.07; 2.2 and 2.46(2H); 3.48(1H); 5.26(2H); 5.89; 6.17 and 6.95(1H); 7.28(3H); |
| 288 | A[21] | Br | isopropyl | H | H | (300, CDCl$_3$); 0.76(3H); 0.98(3H); 1.24(6H); 2.47(1H); 3.46(1H); 4.2(1H); 5.25(2H); 6.18(2H); 6.8(2H); 7.07(1H); 7.24(2H); |
| 289 | A[2] | Br | cyclopentyl | H | H | |
| 290 | A[15] | Br | tert-butyl | H | H | |
| 291 | A[3] trans | OC$_2$H$_5$ | methyl | H | H | (300, CDCl$_3$)1.19–1.45(9H); 1.82(1H); 2.3(3H); 2.45(1H); 3.91(2H); 5.22(2H); 6.13(1H); 7.02(1H); 7.14–7.26(2H) |
| 292 | A[3] | OC$_2$H$_5$ | cyclohexyl | H | H | |
| 293 | A[21] | OC$_2$H$_5$ | cyclopropyl | H | H | |
| 294 | A[4] | OC$_2$H$_5$ | cyclohexyl | CN | H | |
| 295 | A[15] | OC$_2$H$_5$ | cyclohexyl | ethynyl | H | |
| 296 | A[2] | Br | methyl | H | H | |
| 297 | A[2] | Br | cyclopropyl | H | H | |
| 298 | A[21] | OC$_2$H$_5$ | cyclohexyl | H | H | |
| 299 | A[21] | OC$_2$H$_5$ | methyl | H | H | |
| 300 | A[3] trans | OCH$_3$ | methyl | H | H | (300, CDCl$_3$)1.22(3H); 1.34(3H); 1.82(1H); 2.34(3H); 2.43(1H); 3.78(3H); 5.23(2H); 6.14(1H); 7.04(1H); 7.16–7.32(2H) |
| 301 | A[15] | OCH$_3$ | methyl | H | H | |
| 302 | A[2] | OCH$_3$ | cyclohexyl | H | H | (300, CDCl$_3$); 1.15–1.32(6H); 1.42(6H); 1.63–2.38(2H+4H); 2.94(1H); 3.77(3H); 5.2(2H); 5.6 and 6.31(1H); 7.07–7.28(3H) |
| 303 | A[3] | OCH$_3$ | cyclohexyl | H | H | |
| 304 | A[2] | Br | tert-butyl | H | H | |
| 305 | A[3] | Br | sec-butyl | H | H | |
| 306 | A[21] | Br | cyclohexyl | H | H | |
| 307 | A[2] | OCH$_3$ | tert-butyl | H | H | |
| 308 | A[3] | OCH$_3$ | tert-butyl | H | H | |
| 309 | A[2] | OCH$_3$ | methyl | H | H | (300, CDCl$_3$)1.16–1.35(6H); 1.64; 1.88, 2.03 and one partially masked signal(2H); 2.33(3H); 3.77(3H); 5.19(2H); 5.6 and 6.3(1H); 7.03(1H); 7.14–7.26(2H); |
| 310 | A[8] | OCH$_3$ | tert-butyl | H | H | |
| 311 | A[2] | OC$_2$H$_5$ | tert-butyl | H | H | |
| 312 | A[3] | OC$_2$H$_5$ | isopropyl | H | H | |
| 313 | A[2] | OC$_2$H$_5$ | isopropyl | H | H | |
| 314 | A[21] | OC$_2$H$_5$ | isopropyl | H | H | |
| 315 | A[3] | OC$_2$H$_5$ | tert-butyl | H | H | |
| 316 | A[2] | OCH$_3$ | isopropyl | H | H | |
| 317 | A[3] | OCH$_3$ | isopropyl | H | H | |
| 318 | A[21] | OCH$_3$ | isopropyl | H | H | |
| 319 | A[2] | OCH$_3$ | cyclopropyl | H | H | |
| 320 | A[2] | Cl | isopropenyl | H | H | |
| 321 | A[3] | Cl | isopropenyl | H | H | |

TABLE-continued

| No. | A[n*] | R[1] | R[2] | R[3] | X | Physical data <br> $^1$H-NMR: (MHz, LM) δ [ppm] <br> melting point [°C], refractive index |
|---|---|---|---|---|---|---|
| 322 | A[2] | F | isopropenyl | H | H | |
| 323 | A[21] | F | isopropenyl | H | H | |
| 324 | A[2] | CH$_3$ | 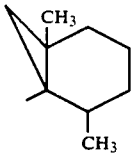 | H | H | |
| 325 | A[4] | CH$_3$ | 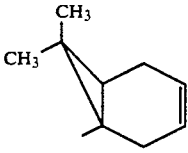 | H | H | |
| 326 | A[2] | Cl | 3,5-diethylcyclohexyl | H | H | |
| 327 | A[2] | CH$_3$ | —CH=C(CH$_3$)$_2$ | H | H | (200, CDCl$_3$); 1.17–1.32(6H); 1.62(3H); 1.9(3H); 1.86–2.3(2H); 2.21(3H); 5.13(2H); 5.6 and 6.3(1H); 6.22(1H); 7.1–7.27(3H); |
| 328 | A[20] | F | isopropyl | H | H | (200, CDCl$_3$); 1.01(6H); 1.27(6H); 2.17(1H); 3.28(1H); 3.96(1H); 5.26(2H); 6.65(2H); 7.2–7.47(5H); mp: 79° C. |
| 329 | A[20] | Cl | isopropyl | H | H | 57–59° C. |
| 330 | A[2] | CH$_3$ | isopropenyl | CH=CH$_2$ | H | $n_D^{22}$: 1.5341 |
| 331 | A[3] | CH$_3$ | isopropenyl | CH=CH$_2$ | H | $n_D^{22}$: 1.4958 |
| 332 | A[20] | CH$_3$ | norborn-2-yl | H | H | (300, CDCl$_3$); 0.98(6H); 1.18–1.67(7H); 1.91(1H); 2.1–2.41(3H); 2.21(3H); 3.42(1H); 3.93(1H); 4.46(1H); 5.19(2H); 6.63(2H); 7.17(2H); 7.28(1H); 7.37(2H) |
| 333 | A[20] | CH$_3$ | isopropenyl | H | H | 98° C. |
| 334 | A[21] | CH$_3$ | isopropenyl | H | H | $n_D^{22}$: 1.5263 |
| 335 | A[2] | CH$_3$ | —C(C$_2$H$_5$)=CH—CH$_3$ | CN | H | $n_D^{22}$: 1.5315 |
| 336 | A[3] | CH$_3$ | —C(C$_2$H$_5$)=CH—CH$_3$ | H | H | $n_D^{22}$: 1.4955 |
| 337 | A[1] | CH$_3$ | —C(C$_2$H$_5$)=CH—CH$_3$ | H | H | $n_D^{22}$: 1.5151 |
| 338 | A[8] | CH$_3$ | —C(C$_2$H$_5$)=CH—CH$_3$ | H | H | $n_D^{22}$: 1.5370 |
| 339 | A[20] | CH$_3$ | —C(C$_2$H$_5$)=CH—CH$_3$ | H | H | 83° C. |
| 340 | A[21] | CH$_3$ | —C(C$_2$H$_5$)=CH—CH$_3$ | H | H | $n_D^{22}$: 1.5229 |
| 341 | A[8] | CH$_3$ | vinyl | H | H | $n_D^{22}$: 1.5535 |
| 342 | A[28] | CH$_3$ | isopropyl | H | H | (200, CDCl$_3$); 1.13–1.42(12H); 1.7; 1.95 and 2 partially masked signals(2H); 2.26(3H); 3.23(1H); 4.26–4.52(1H); 5.19(2H); 7.18–7.36(3H) |
| 343 | A[18] | F | isopropyl | H | H | $n_D^{23}$: 1.5050 |
| 344 | A[18] | CH$_3$ | isopropenyl | H | H | $n_D^{23}$: 1.5220 |
| 345 | A[29] | CH$_3$ | —C(C$_2$H$_5$)=CH—CH$_3$ | H | H | $n_D^{23}$: 1.5196 |
| 346 | A[29] | CH$_3$ | isopropyl | H | H | $n_D^{23}$: 1.5132 |
| 347 | A[18] | CH$_3$ | —C(C$_2$H$_5$)=CH—CH$_3$ | H | H | (300, CDCl$_3$); 0.84–1.12(3H+6H); 1.3 and 1.78(3H); 2.1–2.4(3H+1H+2H); 3.98(1H); 5.08–5.32 and 5.57(2H+1H+1H); 6.6(1H); 6.98–7.34(4H); 7.49(1H) |
| 348 | A[18] | Cl | tert.-butyl | H | H | (300, CDCl$_3$); 1.04(6H); 1.5(9H); 2.26(1H); 4.0(1H); 5.06(1H); 5.3(2H); 6.62(1H); 7.2(2H); 7.31(1H); |

TABLE-continued

| No. | A[n*] | R[1] | R[2] | R[3] | X | Physical data<br>$^1$H-NMR: (MHz, LM) δ [ppm]<br>melting point [°C], refractive index |
|---|---|---|---|---|---|---|
| 349 | A[20] | Cl | tert.-butyl | H | H | 7.44(1H); 7.52(1H)<br>(300, CDCl3); 1.02(6H); 1.48(9H); 1.19(1H); 3.97(1H);<br>4.48(1H); 5.29(2H); 6.64(2H); 7.18(2H); 7.37-7.43(3H); |
| 350 | A[2] | CH3 | —CH(C2H5)2 | CN | H | (200, CDCl3); 0.81(6H); 1.22-1.4(6H); 1.47-1.85(4H);<br>1.98; 2.15 and 2 partially masked signals(2H);<br>2.36(3H); 2.88(1H); 5.69 and 6.27(1H); 6.64(1H);<br>7.33(2H); 7.5(1H); |
| 351 | A[8] | CH3 | —CH(C2H5)2 | H | H | (200, CDCl3); 0.65-0.8(3H+6H); 1.0(3H);<br>1.43-1.78(4H); 2.13(3H); 2.32(1H); 2.78(1H); 3.2(1H);<br>5.14(2H); 7.13(2H); 7.29(4H); |
| 352 | A[18] | CH3 | —CH(C2H5)2 | H | H | (300, CDCl3); 0.77(6H); 0.93-1.07(6H); 1.53(2H);<br>1.67(2H); 2.22(3H+1H); 2.79(1H); 3.98(1H); 5.13(1H);<br>5.22(2H); 6.6(1H); 7.13(3H); 7.3(1H); 7.49(1H); |
| 353 | A[2] | CH3 | —C(CH3)(CH3)(C2H5) | CN | H | (200, CDCl3)0.67(3H); 1.18-1.35(6H); 1.4(6H);<br>1.71; 2.13; 2.32 and one masked signal(2H)<br>1.83(2H); 2.48(3H); 5.61 and 6.2(1H); 6.6(1H);<br>7.17-7.27(1H); 7.4-7.55(2H); |
| 354 | A[2] | CH3 | —C(CH3)(CH3)(C2H5) | H | H | (200, CDCl3)0.67(3H); 1.14-1.3(6H); 1.41(6H);<br>1.66; 2.02; 2.27 and one masked signal(2H);<br>1.83(2H); 2.43(3H); 5.14(2H); 5.6 and 6.29(1H);<br>7.07-7.27(2H); 7.32(1H); |
| 355 | A[3] | CH3 | —C(CH3)(CH3)(C2H5) | H | H | (200, CDCl3)0.67(3H); 1.17-1.36(6H); 1.4(6H);<br>1.83(2H); 1.43(3H); 2.02; 2.18; 2.38-2.53 and one<br>partially masked signal(2H); 5.7(2H);<br>6.12 and 6.95(1H); 7.08-7.23(2H); 7.32(1H) |
| 356 | A[8] | CH3 | —C(CH3)(CH3)(C2H5) | H | H | (200, CDCl3)0.65(3H+3H); 1.02(3H); 1.35(3H);<br>1.8(2H); 2.21-2.4(1H); 2.28(3H); 3.18(1H);<br>5.09(2H); 7.05-7.37(7H); |
| 357 | A[2] | CH3 | isopropyl | CH3 | H | (300, CDCl3); 1.1-1.32(12H); 1.5(3H); 1.87; 1.9;<br>2.0 and one partially masked signal(2H); 2.33(3H);<br>3.22(1H); 5.6 u. 6.3(1H); 6.18(1H); 7.11-7.32(32H); |
| 358 | A[3] | CH3 | isopropyl | CH3 | H | (300, CDCl3); 1.17-138(12H); 1.52(3H); 1.83; 2.04;<br>2.14 and one masked signal(2H); 1.83; 2.04;<br>3.23(1H); 6.2(1H); 6.2; 7.89 and 7.98(1H);<br>7.12-7.34(3H); |
| 359 | A[8] | CH3 | isopropyl | CH3 | H | (300, CDCl3); 0.7(3H); 0.97 and 1.03(3H); 1.18(6H);<br>1.4 and 1.5(3H); 2.16 and 2.35(3H); 2.3(1H); 3.18(1H);<br>6.1(1H); 6.99-7.3(7H); |
| 360 | A[2] cis | CH3 | isopropyl | H | H | (300, CDCl3); 1.16-1.34(12H); and 2.04(2H);<br>2.31(3H); 3.23(1H); 5.16(2H); 6.3(1H); 7.14-7.31(3H); |
| 361 | A[2] trans | CH3 | isopropyl | H | H | (300, CDCl3); 1.16-1.34(12H); 1.66 and 2.25-2.36(2H);<br>2.31(3H); 3.23(1H); 5.16(2H); 5.61(1H); 7.14-7.31(3H); |
| 362 | A[5] | CH3 | isopropyl | H | H | (300, CDCl3); 1.1-1.28(6H); 1.52; 1.74-1.88 and<br>2.02(2H); 2.29(3H); 3.23(1H); 3.97-4.08 and<br>4.63-4.77(1H); 5.14(2H); 7.14-7.29(3H) |
| 363 | A[5] | CH3 | isopropenyl | H | H | (300, CDCl3); 1.09-1.32(6H); 1.53; 1.77-1.9 and one<br>partially masked signal(2H); 2.02(3H); 2.28(3H);<br>3.98-4.1 and 4.62-4.75(1H); 4.83(1H); 5.14;<br>(2H); 5.21(1H); 7.08-7.23(3H); |
| 364 | A[21] | F | tert-butyl | H | H | (200, CDCl3); 0.73(3H); 0.95(3H); 1.4(9H); 2.42(1H);<br>4.18(1H); 5.22(2H); 6.18(2H); 6.81(2H); 7.0-7.37(3H); |
| 365 | A[3] | F | isopropyl | CN | H | (300, CDCl3); 1.2-1.42(12H); 1.75-2.56(2H); 3.28(1H);<br>5.9; 6.17 and 6.78(1H); 6.63(1H); 7.21(1H); 7.43(2H); |
| 366 | A[29] | Cl | isopropyl | H | H | (200, CDCl3); 0.83(3H); 1.02(3H); 1.27(6H); 2.6(1H);<br>3.5(1H); 4.82(1H); 5.35(2H); 6.38(1H); 7.18-7.4(3H);<br>7.6(1H); 7.74(1H); |
| 367 | A[30] | F | isopropyl | H | H | (300, CDCl3); 0.8(3H); 0.98(3H); 1.26(6H); 2.42(1H);<br>3.25(1H); 4.36(1H); 5.24(2H); 7.09(4H); 7.27(1H);<br>7.6(1H); |
| 368 | A[8] | Cl | tert-butyl | H | H | (300, CDCl3); 0.7(3H); 1.03(3H); 1.48(9H); 2.34(1H);<br>3.23(1H); 5.23(2H); 7.1(2H); 7.28(4H); 7.39(1H); |
| 369 | A[3] | Br | isopropyl | CN | H | (300, CDCl3); 1.2-1.42(12H); 1.8; 1.88; 2.0; 2.08;<br>2.29 u. 2.51(2H); 3.47(1H); 5.9; 6.16 u. 6.88(1H);<br>6.8(1H); 7.42(2H); 7.61(1H); |
| 370 | A[2] | Br | isopropyl | sopropyl | H | (200, CDCl3); 1.18-1.36(18H); 1.63-2.4(3H); 3.47(1H);<br>5.23(1H); 5.62 and 6.29(1H); 7.28(3H); |
| 371 | A[3] | Cl | methyl | H | H | (200, CDCl3); 1.2-1.38(6H); 1.78; 1.87; 1.99; 2.07;<br>2.21 and one partially masked signal(2H);<br>2.42(3H); 5.27(2H); 5.91; 6.17 and 6.96(1H); 7.24(3H); |
| 372 | A[21] | OCH3 | cyclohexyl | H | H | (200, CDCl3); 0.8(3H); 1.02(3H); 1.44(6H); 1.87(4H); |

TABLE-continued

| No. | A^(n*) | R^1 | R^2 | R^3 | X | Physical data ^1H-NMR: (MHz, LM) δ [ppm] melting point [°C.]. refractive index |
|---|---|---|---|---|---|---|
| 373 | A^2 | Cl | isopropyl | H | 4-Cl | 2.46(1H); 2.97(1H); 3.73(3H); 4.2(1H); 5.27(2H); 6.2(2H); 6.82(2H); 7.13(2H); 7.3(1H); (300, CDCl3): 1.17–1.48(12H); 1.71; 1.94; 2.07 and 2.28(2H); 3.94(1H); 5.2(2H); 5.63 and 6.27(1H); 7.08–7.31(2H); |
| 374 | A^3 | Cl | isopropyl | H | 4-Cl | (300, CDCl3); 1.23–1.47(12H); 1.87; 2.09; 2.21 and 2.46(2H); 3.95(1H); 5.21(2H); 6.16 and 6.92(1H); 7.13–7.31(2H); |
| 375 | A^2 | Cl | n-utyl | H | 4-Cl | (300, CDCl3); 0.95(3H); 1.19–1.6(6H+4H); 1.7; 1.93; 2.08 amd 2.28(2H); 2.94(2H); 5.19(2H); 5.62 and 6.26(1H); 7.18(1H); 7.28(1H); |
| 376 | A^3 | Cl | n-utyl | H | 4-Cl | (300, CDCl3); 0.97(3H); 1.21–1.61(6H+4H); 1.77; 1.85; 1.99; 2.07; 2.2 u. 2.45(2H); 2.93(2H); 5.2(2H); 5.9; 6.17; 6.62 and 6.92(1H); 7.18(1H); 7.28(1H) |

*)A^n ( n = 1–27) stands for the carboxylate radical of a pyrethroid acid (A^n—H) mentioned in the above text Preparation of starting materials in accordance with German Application No. P 38 20 896.

1-(3'-Chloro-2'-methylphenyl)-cyclohexanol

Under a nitrogen blanket, 96 g (4 moles) of magnesium shavings in 60 ml of absolute THF (tetrahydrofuran) are placed in a receiver. At 65° C., 1 ml of 1,2-dibromoethane is added and then a solution of 644 g (4 moles) of 2,6-dichlorotoluene in 1.5 liters of absolute THF is dripped in over a period of 2¼ hours. The mixture is then stirred under reflux for 4 hours and cooled to room temperature, and 352.8 g (3.6 moles) of cyclohexanone in 250 ml of absolute THF is added under a nitrogen blanket. After the reaction the Grignard reaction mixture is worked up as usual and the solvent is substantially removed by distillation under reduced pressure. The residue is subjected to incipient distillation (30° to 107° C./0.27 mbar). The crude product remaining (676 g), which already consists to the extent of 90% of 1-(3'-chloro-2'-methylphenyl)-cyclohexanol, can be purified further by column chromatography using toluene as eluant.

3-Cyclohexyl-2-methylchlorobenzene 103 g of 1-(3'-chloro-2'-methylphenyl)-cyclohexene is dissolved in 1,200 ml of ethanol; 5 g of Pd/charcoal is then added. Hydrogenation is then carried out for 8 hours at room temperature and a hydrogen pressure of 80 bar. The catalyst is filtered off and the remaining solution is evaporated down. Fractional distillation gives 51.8 g of 3-cyclohexyl-2-methylchlorobenzene.

3-(1'-Cyclohexenyl)-2-methylbenzonitrile 250 g (0.6 mol) of 1-(3'-chloro-2'-methylphenyl)-cyclohexene, 600 ml of 1-methyl-2-pyrrolidone and 63 g of anhydrous copper(I) cyanide are boiled for 35 hours with stirring. The reaction mixture is poured into a solution of 500 ml of ethylenediamine in 1.5 liters of water and the whole stirred for 45 minutes at 50° C., followed by repeated extraction with toluene. The combined organic phases are extracted by shaking with 10% strength sodium cyanide solution, followed by drying over Na2SO4 and concentration. Purification by column chromatography over silica gel with toluene/cyclohexane (3/7) as eluant gives 117.8 g of the nitrile (mp: 54°–57° C.).

USE EXAMPLES

In the following examples, the following compounds A and B were used for comparison purposes:

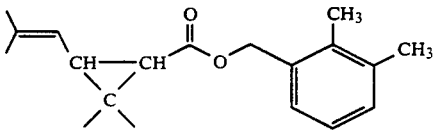

disclosed in Pestic. Sci. 1(2), 49–52, 1970 and Pestic. Sci. 3(1), 25–28, 1972

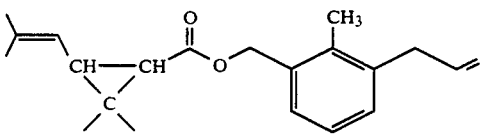

disclosed in DE-OS 33 27 292, Ex. 26

The comparative agents were more than 95% pure.

The concentrations at which the compounds investigated had 100% or 80% kill or inhibition are the minimum concentrations (action threshold). At least two experiments were run for each concentration, and an average was formed.

Contact action on oriental cockroaches (Blatta orientalis)

The bottoms of a 1-liter jars were treated with acetonic solutions of the active ingredients. After the solvent had evaporated, 5 adult cockroaches were introduced into each jar.

The kill rate was determined after 48 hours.

The compounds of Examples 2 (cis/trans = 15/85), 13, 65 and 119 achieved 100% kill at a concentration of 0.2 mg. At lower concentrations of 0.2 to 0.04 mg, compounds 2 (cis), 77, 107 and 210 achieved kill rates of from 60 to 100%. Comparative compounds A and B were ineffective at a concentration of 1 mg.

Contact action on granary weevils (Sitophilus granaria)

Roughened glass plates 8×8 cm were treated with acetonic solutions of the active ingredients.

After the solvent had evaporated, 100 weevils were placed on each plate and covered with a watchglass 6 cm in diameter. After 4 hours the weevils were transferred to untreated vessels. The kill rate was determined after 24 hours by ascertaining how many weevils were able, after this length of time, to leave within 60 minutes an untreated cardboard dish (40 mm in diameter and 10 mm high).

The compounds of Examples 1, 2 (cis), 2 (cis, trans=15/85), 5, 107, 173, 193, 204, 210 and 268 achieved kill rates of from 0 to 100% at concentrations of from 0.04 to 0.4 mg. Comparative compounds A and B were ineffective at a concentration of 1 mg.

Contact action on yellow fever mosquito (*Aedes aegypti*)

The active ingredient formulations were added to 200 ml of tapwater in 250 ml plastic beakers, and 20 to 30 mosquito larvae in the 3rd to 4th larval stage were introduced.

The temperature was kept at 25° C. The action was assessed after 24 hours.

The active ingredients of Examples 2 (cis/trans=15/85), 2 (cis), 5, 107, 113, 119, 173 and 179 achieved approximately 80% kill at concentrations of 0.02 ppm, 0.01 ppm and less. Comparative compounds A and B were ineffective at a concentration of 0.1 ppm.

Continuous contact action on houseflies (*Musca domestica*)

Both tops and bottoms of Petri dishes 10 cm in diameter were lined with a total of 2 ml of acetonic active ingredient solutions. After the solvent had evaporated (about 30 mins.) 10 flies were introduced into each dish. The kill rate was assessed after 4 hours.

The active ingredients of Examples 1, 2 (cis/trans=15/85), 5, 107, 113, 119, 173, 179 and 210 achieved a kill rate of about 80 to 100% at concentrations ranging from 0.004 to 0.001 mg. Comparative substance A gave a kill rate of about 80% when applied at a rate of 0.1 mg, and comparative substance B achieved 100% kill at this concentration.

Contact action on ticks (*Ornithodorus moubata*)

Young ticks (1.5 to 2 mm in diameter) which had sucked blood once were individually picked up by means of a suction tube. A strong light source drove the active animals from the discarded exoskeleton remains.

5 ticks were placed in bags which let liquid through, and the bags were dipped for 5 seconds in aqueous active ingredient formulations. The bags were then suspended and the action was assessed after 48 hours by placing the bags on a hotplate; the animals still living were easy to recognize from their movements.

The compounds of Examples 18, 193, 210 and 268 achieved 60 to 80% kill at concentrations of from 0.4 to 4 ppm. Compounds 5 and 13 achieved 100% kill at concentrations of 5 and 10 ppm. Comparative substance A only achieved 100% kill at the much higher concentration of 400 ppm, and comparative substance B was ineffective at as high a rate as 1,000 ppm.

Effect of ingested food on caterpillars of the diamondback moth (*Plutella maculipennis*)

Leaves of young cabbage plants were dipped for 3 seconds in aqueous emulsions of the active ingredients and were placed, after excess liquid had been briefly allowed to drip off, on a moist filter paper in a Petri dish. 10 caterpillars of the 4th stage were then placed on each leaf.

The action was assessed after 48 hours.

The compounds of Examples 1, 5, 18, 107, 119, 179, 204 and 268 achieved kill rates of 80 to 100% at concentrations of 0.4 to 20 ppm. At concentrations of 40 ppm, compounds 13, 60, 65 and 193 achieved kill rates of 60 to 100%. Comparative substance A achieved 100% kill only at a rate of 400 ppm, and comparative substance B gave 100% kill at a rate of 40 ppm.

Contact action on cotton stainers (*Dysdercus intermedius*)

Petri dishes 10 cm in diameter were lined with 1 ml of acetonic solutions of the active ingredients. After the solvent had evaporated, 20 larvae of the penultimate stage were placed in each dish. The action was assessed after 24 hours.

The compounds of Examples 1, 2 (cis), 2 (cis/trans=15/85), 107, 113, 179 and 204 achieved 100% kill at concentrations of 0.1 to 1 ppm. Comparative compounds A and B were ineffective at a concentration of 10 ppm.

Contact action on *Prodenia litura*

The bottoms of Petri dishes 10 cm in diameter were treated with acetonic solutions of the active ingredients. After the solvent had evaporated, 5 caterpillars of the 3rd stage were placed in each dish, and the dishes were closed. The kill rate was assessed after 4 hours.

The compounds of Examples 2 (cis/trans=15/85), 5, 107, 113, 119, 179, 204 and 268 achieved approx. 80% kill at concentrations ranging from 0.01 to 0.001 mg. The cis isomer 2 achieved 100% kill at a concentration of 0.001 mg. The comparative agents achieved 100% kill at concentrations of 0.02 mg (A) and 0.04 mg (B).

We claim:

1. A benzyl ester of the formula

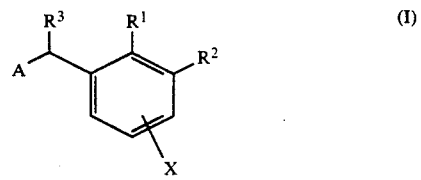

wherein $R^1$ is methyl, ethyl, halogen, methoxy or ethoxy; $R^2$ is straight-chain or branched $C_1$–$C_{20}$-alkyl, straight-chain or branched $C_2$–$C_{20}$-alkenyl, $C_3$–$C_8$-cycloalkyl, $C_3$–$C_8$-cycloalkenyl, $C_5$–$C_{12}$-bicycloalkyl, $C_5$–$C_{12}$-bicycloalkenyl, $C_1$–$C_5$-alkyl-substituted $C_3$–$C_8$-cycloalkyl, $C_1$–$C_5$-alkyl-substituted $C_3$–$C_8$-cycloalkenyl, $C_1$–$C_5$-alkyl-substituted $C_5$–$C_{12}$-bicycloalkyl, or $C_1$–$C_5$-alkyl-substituted $C_5$–$C_{12}$-bicycloalkenyl; $R^3$ is hydrogen; A is the carboxylate radical of an acid selected from the group consisting of 3-(2′, 2′-dimethylvinyl)-2,2-dimethylcyclopropane-1-carboxylic acid, 3-(2′, 2′-dichlorovinyl)-2,2-dimethylcyclopropane-1-carboxylic acid, 3-(2′-chloro-3′,3′,3′-trifluoroprop-1′-enyl)-2,2-dimethylcyclopropane-1-carboxylic acid, 3-(2′,2′-dibromovinyl)-2,2-dimethylcyclopropane-1-carboxylic acid, 3-(2′,2′-difluorovinyl)-2,2-dimethylcyclopropane-1-carboxylic acid, 3-(2′-fluoro-3′,3′,3′-trifluoroprop-1′-enyl)-2,2-dimethylcyclopropane-1-carboxylic acid, 3-(2′,2′-bistrifluoromethylvinyl)-2,2-dimethylcyclopropane-1-carboxylic acid, 2-(4′-chlorophenyl)-3-methylbutyric acid, 2-(4′-fluorophenyl)-3-methylbutyric acid, 2-(4′-difluoromethoxyphenyl)-3-methylbutyric acid, 3-(4′-tert-butylphenyl)-2,2-dimethylcyclopropane-1-carboxylic acid, 2,2,3,3-tetramethylcyclopropane-1-carboxylic acid, 1-(4′-chlorophenyl)-cyclopropane-1-carboxylic acid, 1-(4′-ethoxyphenyl)-2,2-dichlorocyclopropane-1-carboxylic acid, 3-[2′-(4″-chlorophenyl)-2′-chlorovinyl]-2,2-dimethylcyclopropane-1-carboxylic acid, 3-(1′,3-butadienyl)-2,2-dimethylcyclopropane-1-carboxylic acid, 3-(2′-methyl-2′-methoxycarbonylvinyl)-2,2-dimethylcyclopropane-1-carboxylic acid, 2-(2′-chloro-4′-trifluoromethylphenylamino)-3-methylbutyric acid, 2-(2′-fluoro-4′-trifluoromethylphenylamino)-3-methylbutyric acid, 3-methyl-2-(4′-trifluoromethylphenylamino)butyric acid, 3-methyl-2-(pyrrol-1'-yl)-butyric acid, 3-methyl-2-(3'-methylpyrrol-1-yl)-butyric acid, 2-(3',4-'dimethylpyrrol-1'-yl)-3-methylbutyric acid, 2-(2'-5'-dimethylpyrrol-1'-yl)-3-methylbutyric acid, 2-(isoindolin-2-yl)-3-methylbutyric acid, 1,1-dimethyl-2,2[H]indenespirocyclopropane-3-carboxylic acid, 3-cyclopentylidenemethyl-2,2-dimethylcyclopropane-1-carboxylic acid, 3-(1',2'-dibromo-2',2'-dichloroethyl)-2,2-dimethylcyclopropane-1-carboxylic acid, 3methyl-2-(pyrazol-1'-yl)-butyric acid, and 3-methyl-2-(imidazol-1-yl)-butyric acid; and X is hydrogen or halogen; with the proviso that $R^2$ is not $CH_2—CH=CH—B$ when B is hydrogen, alkyl or alkenyl and at the same time $R^1$ is methyl or halogen, and furthermore with the proviso that $R^2$ is not methyl when $R^1$ is methyl.

2. The benzyl ester of claim 1, wherein $R^2$ is a branched alkyl or alkenyl group having 3 to 8 carbon atoms.

3. The benzyl ester of claim 1, wherein $R^2$ is selected from the group consisting of isopropyl, isopropenyl, secbutyl, tert-butyl, 1-buten-2-yl, 2-butenyl, 1,3-butadienyl isopentyl, sec-pentyl 3-penten-2-yl, 1-penten-2-yl and sec-hexyl.

4. The benzyl ester of claim 1, wherein X is hydrogen and $R^1$ is methyl, chlorine, fluorine or bromine.

5. The benzyl ester of claim 1, wherein X is hydrogen.

6. The benzyl ester of claim 1, wherein A is the carboxylate radical of an acid selected from the group consisting of 3-(2',2'-dichlorovinyl)-2,2-dimethylcyclopropane-1-carboxylic acid, 3-(2'-chloro-3',3',3'-trifluoroprop-1'-enyl)-2,2-dimethylcyclopropane-1-carboxylic acid, 3-methyl-2-(pyrrol-1'-yl)-butyric acid, 3-methyl-2-(3'-methylpyrrol-1'-yl)-butyric acid, 2-(3',4'-dimethylpyrrol-1'-yl)-3-methylbutyric acid, and 2-(2'-5'-dimethylpyrrol-1'-yl)-3-methylbutyric acid.

7. The benzyl ester of claim 1, wherein $R^1$ is methyl.

8. The benzyl ester of claim 1, wherein $R^1$ is chloro.

* * * * *